US012575742B2

(12) United States Patent
Hocking et al.

(10) Patent No.: US 12,575,742 B2
(45) Date of Patent: Mar. 17, 2026

(54) NON-INVASIVE VENOUS WAVEFORM ANALYSIS FOR EVALUATING A SUBJECT

(71) Applicant: Vanderbilt University, Nashville, TN (US)

(72) Inventors: Kyle M. Hocking, Nashville, TN (US); Colleen M. Brophy, Nashville, TN (US); Susan S. Eagle, Nashville, TN (US); Grant Hocking, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1086 days.

(21) Appl. No.: 17/054,101

(22) PCT Filed: May 10, 2019

(86) PCT No.: PCT/US2019/031655
§ 371 (c)(1),
(2) Date: Nov. 9, 2020

(87) PCT Pub. No.: WO2019/217778
PCT Pub. Date: Nov. 14, 2019

(65) Prior Publication Data
US 2021/0298610 A1     Sep. 30, 2021

Related U.S. Application Data

(60) Provisional application No. 62/669,659, filed on May 10, 2018.

(51) Int. Cl.
*A61B 5/00*     (2006.01)
*A61B 5/02*     (2006.01)
*A61B 5/0295*   (2006.01)

(52) U.S. Cl.
CPC ...... *A61B 5/02007* (2013.01); *A61B 5/02014* (2013.01); *A61B 5/0295* (2013.01);
(Continued)

(58) Field of Classification Search
None
See application file for complete search history.

(56) References Cited

U.S. PATENT DOCUMENTS

| | | | | |
|---|---|---|---|---|
| 2001/0037056 A1* | 11/2001 | Nunome | ............... | A61B 5/318 |
| | | | | 600/300 |
| 2002/0095090 A1* | 7/2002 | Caro | ...................... | A61B 5/022 |
| | | | | 600/485 |

(Continued)

FOREIGN PATENT DOCUMENTS

| | | |
|---|---|---|
| JP | 2006-526460 A | 11/2006 |
| KR | 20170124943 | 11/2017 |

OTHER PUBLICATIONS

Chang et al., "Quantitative Non-stationary Assessment of Cardiovascular Diseases based on Arterial Blood Pressure Waveform by using Hilbert-Huang Transform", 2013 9th International Conference on Information, Communications & Signal Processing, IEEE, 2013, 1-5.

(Continued)

*Primary Examiner* — Etsub D Berhanu
(74) *Attorney, Agent, or Firm* — McDonnell Boehnen Hulbert & Berghoff LLP

(57)     ABSTRACT

A method embodiment includes generating, via a sensor of a computing device, a signal representing vibrations originating from a blood vessel of a subject and decomposing the signal into one or more first intrinsic oscillatory modes and one or more second intrinsic oscillatory modes. The one or more first intrinsic oscillatory modes have respective oscillation frequencies that are less than respective oscillation frequencies of the one or more second intrinsic oscillatory (Continued)

modes. The method includes obtaining an intensity spectrum of the one or more first intrinsic oscillatory modes over a range of frequencies and using the obtained intensity spectrum to determine a blood volume status of the subject. Another method embodiment includes using the one or more second intrinsic oscillatory modes to determine one or more mechanical properties of the blood vessel or tissue adjacent to the blood vessel.

19 Claims, 20 Drawing Sheets

(52) U.S. Cl.
CPC .......... *A61B 5/4878* (2013.01); *A61B 5/7253* (2013.01); *A61B 5/7275* (2013.01); *A61B 5/742* (2013.01); *A61B 5/681* (2013.01); *A61B 2562/0247* (2013.01); *A61B 2562/0261* (2013.01)

(56) References Cited

U.S. PATENT DOCUMENTS

| | | | | |
|---|---|---|---|---|
| 2003/0004422 A1* | 1/2003 | Narimatsu | ........... | A61B 5/0285 600/500 |
| 2003/0036685 A1* | 2/2003 | Goodman | .............. | G16H 70/20 600/300 |
| 2003/0069508 A1* | 4/2003 | Kawaguchi | .............. | A61B 8/06 600/500 |
| 2003/0083580 A1* | 5/2003 | Tampo | ................. | A61B 5/7445 600/490 |
| 2003/0130578 A1* | 7/2003 | Narimatsu | ........... | A61B 5/0285 600/438 |
| 2004/0171940 A1* | 9/2004 | Narimatsu | ........... | A61B 5/0285 600/493 |
| 2004/0171956 A1* | 9/2004 | Babashan | .............. | A61B 5/681 600/509 |
| 2007/0032732 A1 | 2/2007 | Shelley et al. | | |
| 2010/0292590 A1* | 11/2010 | Matsukawa | .............. | A61B 7/04 600/500 |
| 2011/0245628 A1 | 10/2011 | Baker, Jr. et al. | | |
| 2014/0288446 A1* | 9/2014 | Lee | ........................ | A61B 5/022 600/493 |
| 2015/0374275 A1* | 12/2015 | Peipsi | .................... | A61B 5/442 600/587 |
| 2016/0270739 A1* | 9/2016 | Wu | ........................ | A61B 5/282 |
| 2017/0079538 A1* | 3/2017 | Liang | .................. | A61B 5/7235 |
| 2017/0209074 A1* | 7/2017 | Siu | ....................... | A61B 5/0873 |
| 2017/0332919 A1 | 11/2017 | Eagle et al. | | |
| 2018/0055445 A1* | 3/2018 | Chang | .................... | A61B 5/024 |

OTHER PUBLICATIONS

Zhang et al., "Arteriosclerosis Feature Extraction for Human Pulse Signals", 2015 International Symposium on Bioelectronics and Bioinformatics (ISBB), IEEE, 2015, 192-195.
Arasteh et al., "Application of Empirical Mode Decomposition in Prediction of Acute Hypotension Episodes", Biomedical Engineering (ICBME), 2010 17th Iranian Conference, IEEE, 2010, 1-4.

* cited by examiner

402 — GENERATING, VIA A SENSOR OF A COMPUTING DEVICE, A SIGNAL REPRESENTING VIBRATIONS ORIGINATING FROM A BLOOD VESSEL OF A SUBJECT

404 — DECOMPOSING THE SIGNAL INTO ONE OR MORE FIRST INTRINSIC OSCILLATORY MODES AND ONE OR MORE SECOND INTRINSIC OSCILLATORY MODES, WHEREIN THE ONE OR MORE FIRST INTRINSIC OSCILLATORY MODES HAVE RESPECTIVE OSCILLATION FREQUENCIES THAT ARE LESS THAN RESPECTIVE OSCILLATION FREQUENCIES OF THE ONE OR MORE SECOND INTRINSIC OSCILLATORY MODES

406 — OBTAINING AN INTENSITY SPECTRUM OF THE ONE OR MORE FIRST INTRINSIC OSCILLATORY MODES OVER A RANGE OF FREQUENCIES

408 — USING THE OBTAINED INTENSITY SPECTRUM TO DETERMINE A BLOOD VOLUME STATUS OF THE SUBJECT

FIG. 4

Time (seconds)

Time (seconds)

NON-INVASIVE VENOUS WAVEFORM ANALYSIS FOR EVALUATING A SUBJECT

CROSS REFERENCE TO RELATED APPLICATION

This application is the US national phase under 35 U.S.C. § 371 of International Application No. PCT/US2019/031655, filed on May 10, 2019, which claims the benefit of U.S. Provisional Patent Application No. 62/669,659, filed on May 10, 2018, the contents of which are incorporated herein by reference in their entirety.

STATEMENT REGARDING FEDERALLY SPONSORED RESEARCH OR DEVELOPMENT

This invention was made with government support under Contract Number 1549576 awarded by the National Science Foundation. The government has certain rights in the invention.

BACKGROUND

Unless otherwise indicated herein, the materials described in this section are not prior art to the claims in this application and are not admitted to be prior art by inclusion in this section.

Some methods of determining blood volume status or related metrics of patient health involve invasive measurement of central venous pressure (CVP) or central arterial pressure (CAP) via insertion of a catheter. Unfortunately, CVP/CAP measurements can be slow to change in response to certain acute conditions and can lead to inadequate fluid administration. Fluid overload detection is difficult, whether caused by excessive fluid administration or pathological conditions. Fluid overload can lead to increased morbidity and mortality. Conventional vital sign monitoring fails to detect euvolemia or hypervolemia during resuscitation, often resulting in unguided and/or excessive fluid administration.

SUMMARY

A first aspect of the disclosure is a method that includes generating, via a sensor of a computing device, a signal representing vibrations originating from a blood vessel of a subject and decomposing the signal into one or more first intrinsic oscillatory modes and one or more second intrinsic oscillatory modes. The one or more first intrinsic oscillatory modes have respective oscillation frequencies that are less than respective oscillation frequencies of the one or more second intrinsic oscillatory modes. The method includes obtaining an intensity spectrum of the one or more first intrinsic oscillatory modes over a range of frequencies and using the obtained intensity spectrum to determine a blood volume status of the subject.

A second aspect of the disclosure is a computing device that includes one or more processors, a sensor, a user interface, and a computer readable medium storing instructions that, when executed by the one or more processors, cause the computing device to perform functions. The functions include generating, via the sensor, a signal representing vibrations originating from a blood vessel of a subject and decomposing the signal into one or more first intrinsic oscillatory modes and one or more second intrinsic oscillatory modes. The one or more first intrinsic oscillatory modes have respective oscillation frequencies that are less than respective oscillation frequencies of the one or more second intrinsic oscillatory modes. The functions include obtaining an intensity spectrum of the one or more first intrinsic oscillatory modes over a range of frequencies and using the obtained intensity spectrum to determine a blood volume status of the subject.

A third aspect of the disclosure is a non-transitory computer readable medium storing instructions that, when executed by a computing device, cause the computing device to perform functions. The functions include generating, via a sensor of the computing device, a signal representing vibrations originating from a blood vessel of a subject and decomposing the signal into one or more first intrinsic oscillatory modes and one or more second intrinsic oscillatory modes. The one or more first intrinsic oscillatory modes have respective oscillation frequencies that are less than respective oscillation frequencies of the one or more second intrinsic oscillatory modes. The functions include obtaining an intensity spectrum of the one or more first intrinsic oscillatory modes over a range of frequencies and using the obtained intensity spectrum to determine a blood volume status of the subject.

A fourth aspect of the disclosure is a method that includes generating, via a sensor of a computing device, a signal representing vibrations originating from a blood vessel of a subject and decomposing the signal into one or more first intrinsic oscillatory modes and one or more second intrinsic oscillatory modes. The one or more first intrinsic oscillatory modes have respective oscillation frequencies that are less than respective oscillation frequencies of the one or more second intrinsic oscillatory modes. The method includes using the one or more second intrinsic oscillatory modes to determine one or more mechanical properties of the blood vessel or tissue adjacent to the blood vessel.

A fifth aspect of the disclosure is a computing device that includes one or more processors, a sensor, a user interface, and a computer readable medium storing instructions that, when executed by the one or more processors, cause the computing device to perform functions. The functions include generating, via the sensor, a signal representing vibrations originating from a blood vessel of a subject and decomposing the signal into one or more first intrinsic oscillatory modes and one or more second intrinsic oscillatory modes. The one or more first intrinsic oscillatory modes have respective oscillation frequencies that are less than respective oscillation frequencies of the one or more second intrinsic oscillatory modes. The functions include using the one or more second intrinsic oscillatory modes to determine one or more mechanical properties of the blood vessel or tissue adjacent to the blood vessel.

A sixth aspect of the disclosure is a non-transitory computer readable medium storing instructions that, when executed by a computing device, cause the computing device to perform functions. The functions include generating, via a sensor of the computing device, a signal representing vibrations originating from a blood vessel of a subject and decomposing the signal into one or more first intrinsic oscillatory modes and one or more second intrinsic oscillatory modes. The one or more first intrinsic oscillatory modes have respective oscillation frequencies that are less than respective oscillation frequencies of the one or more second intrinsic oscillatory modes. The functions include using the one or more second intrinsic oscillatory modes to determine one or more mechanical properties of the blood vessel or tissue adjacent to the blood vessel.

These, as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

BRIEF DESCRIPTION OF THE DRAWINGS

FIG. 4 is a block diagram of a method, according to an example embodiment.

DETAILED DESCRIPTION

Figure 1:
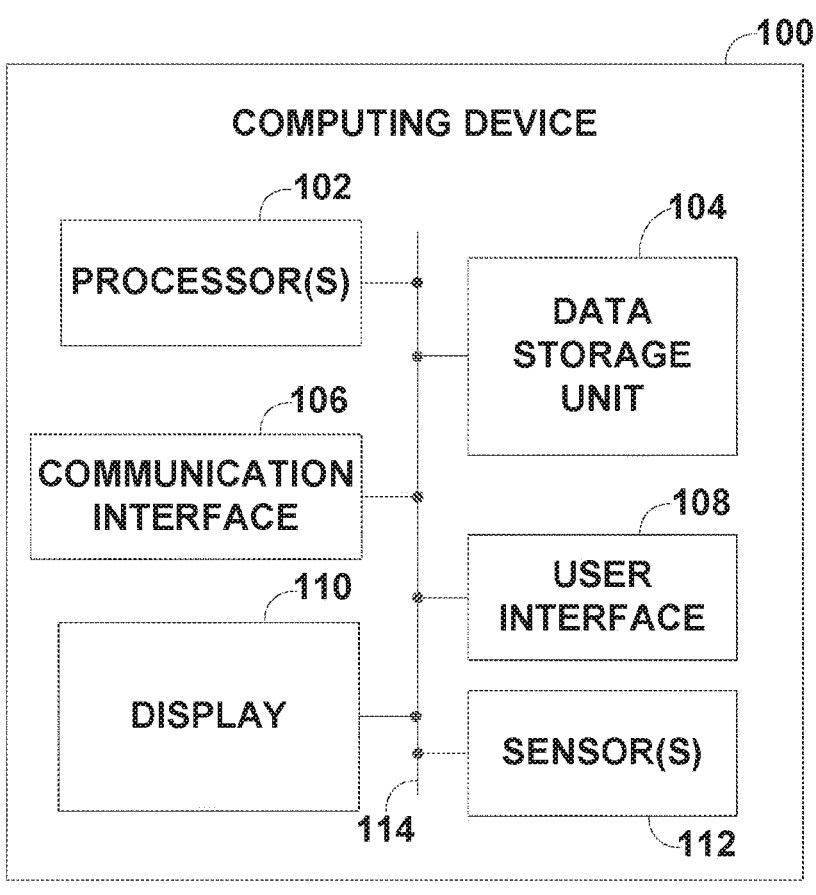
FIG. 1 is a schematic diagram of a computing device, according to an example embodiment.

As discussed above, determination of blood volume status via catheter insertion and measurement of central venous pressure (CVP) or central arterial pressure (CAP) has diagnostic value, but is inherently invasive and can be costly. Disclosed herein are methods and systems for using non-invasive venous waveform analysis (NIVA) to indirectly determine or detect blood volume status, CVP/CAP, mechanical in vivo properties of a subject's blood vessels, the presence of edema in the subject, and other subject metrics such as mean pulmonary arterial pressure, pulmonary artery diastolic pressure, left ventricular end diastolic pressure, left ventricular end diastolic volume, cardiac output, total blood volume, volume overload, dehydration, hemorrhage, and volume responsiveness. One or more of these metrics may be used to diagnose or treat various disorders that may afflict a subject or be used for real time assessment and resuscitation of a subject.

Methods disclosed herein generally involve non-invasively measuring a peripheral arterial waveform (PAW) or a peripheral vein waveform (PVW) using a (e.g., piezoelectric) sensor positioned over a subject's artery or vein (e.g., in contact with the subject's skin). The waveforms represent vibrations originating from the blood vessel of the subject and are generally caused by blood flowing though the vessel and/or the physiological reaction of the vessel or surrounding tissue to the blood flow. The sensor generates a signal representing the vibrations and a computing device can process the signal to decompose the signal into intrinsic oscillatory modes, using empirical mode decomposition (EMD) (e.g., a Hilbert-Huang transform) or ensemble EMD (EEMD). This technique allows for non-linear analysis of the signal, which is useful because the signal representing the blood vessel vibrations will generally take the form of a soliton. By decomposing the waveform, a pulse pressure waveform mode can be isolated from components of the signal representing motion effects and high frequency dissipative shear waves that are generated as a conical wake by the propagating vessel pressure pulse. As such, blood volume status identification can be performed with increased accuracy. In addition, these techniques enable the quantification of blood vessel mechanical properties from the higher order intrinsic oscillatory modes.

In a particular embodiment, the amplitude spectral density of the non-invasive indirect pulse waveform mode is generated by the computing device. The indirect pulse waveform mode generally consists of the full signal minus three to five of the higher order intrinsic oscillatory modes. A ratio of the amplitude of the heart rate and weighted amplitudes of the harmonics of the heart rate divided by the sum of the heart rate and the heart rate harmonics can be normalized to create an "estimated pulmonary capillary wedge pressure which is directly related to the subject's blood volume status. Pulmonary capillary wedge pressure is a well described measure of volume status. The mechanical attenuation properties of the blood vessels can be quantified from the high frequency dissipative shear wave mode. The edema state of the patient can be determined from the decomposed modes of the waveforms.

FIG. 1 is a simplified block diagram of an example computing device 100 that can perform various acts and/or functions, such as any of those described in this disclosure. The computing device 100 may be a mobile phone, a tablet computer, a laptop computer, a desktop computer, a wearable computing device (e.g., in the form of a wrist band), among other possibilities.

The computing device 100 includes one or more processors 102, a data storage unit 104, a communication interface 106, a user interface 108, a display 110, and sensor(s) 112. These components as well as other possible components can connect to each other (or to another device or system) via a connection mechanism 114, which represents a mechanism that facilitates communication between two or more devices or systems. As such, the connection mechanism 114 can be a simple mechanism, such as a cable or system bus, or a relatively complex mechanism, such as a packet-based communication network (e.g., the Internet). In some instances, a connection mechanism can include a non-tangible medium (e.g., where the connection is wireless).

The processor 102 may include a general-purpose processor (e.g., a microprocessor) and/or a special-purpose processor (e.g., a digital signal processor (DSP)). In some instances, the computing device 100 may include more than one processor to perform functionality described herein.

The data storage unit 104 may include one or more volatile, non-volatile, removable, and/or non-removable storage components, such as magnetic, optical, or flash storage, and/or can be integrated in whole or in part with the processor 102. As such, the data storage unit 104 may take the form of a non-transitory computer-readable storage medium, having stored thereon program instructions (e.g., compiled or non-compiled program logic and/or machine code) that, when executed by the processor 102, cause the computing device 100 to perform one or more acts and/or functions, such as those described in this disclosure.

Such program instructions can define and/or be part of a discrete software application. In some instances, the computing device 100 can execute program instructions in response to receiving an input, such as from the communication interface 106 and/or the user interface 108. The data storage unit 104 may also store other types of data, such as those types described in this disclosure.

The communication interface 106 can allow the computing device 100 to connect to and/or communicate with another other device or system according to one or more communication protocols. The communication interface 106 can be a wired interface, such as an Ethernet interface or a high-definition serial-digital-interface (HD-SDI). The communication interface 106 can additionally or alternatively include a wireless interface, such as a cellular or WI-FI interface. A connection provided by the communication interface 106 can be a direct connection or an indirect connection, the latter being a connection that passes through and/or traverses one or more entities, such as such as a router, switcher, or other network device. Likewise, a transmission to or from the communication interface 106 can be a direct transmission or an indirect transmission.

The user interface 108 can facilitate interaction between the computing device 100 and a user of the computing device 100, if applicable. As such, the user interface 108 can include input components such as a keyboard, a keypad, a mouse, a touch sensitive and/or presence sensitive pad or display, a microphone, a camera, and/or output components such as a display device (which, for example, can be combined with a touch sensitive and/or presence sensitive panel), a speaker, and/or a haptic feedback system. More generally, the user interface 108 can include any hardware and/or software components that facilitate interaction between the computing device 100 and the user of the computing device 100.

In a further aspect, the computing device 100 includes the display 110. The display 110 may be any type of graphic display. As such, the display 110 may vary in size, shape, and/or resolution. Further, the display 110 may be a color display or a monochrome display.

The sensor(s) 112 may take the form of a piezoelectric sensor, a pressure sensor, a force sensor, an optical wavelength selective reflectance or absorbance measurement system, a tonometer, an ultrasound probe, a plethysmograph, or a pressure transducer. Other examples are possible. The sensor(s) 112 may be configured to detect vibrations originating from a blood vessel of a subject as further described herein.

As indicated above, the connection mechanism 114 may connect components of the computing device 100. The connection mechanism 114 is illustrated as a wired connection, but wireless connections may also be used in some implementations. For example, the communication mechanism 114 may be a wired serial bus such as a universal serial bus or a parallel bus. A wired connection may be a proprietary connection as well. Likewise, the communication mechanism 114 may also be a wireless connection using, e.g., Bluetooth® radio technology, communication protocols described in IEEE 802.11 (including any IEEE 802.11 revisions), cellular technology (such as GSM, CDMA, UMTS, EV-DO, WiMAX, or LTE), or Zigbee® technology, among other possibilities.

Figure 2:
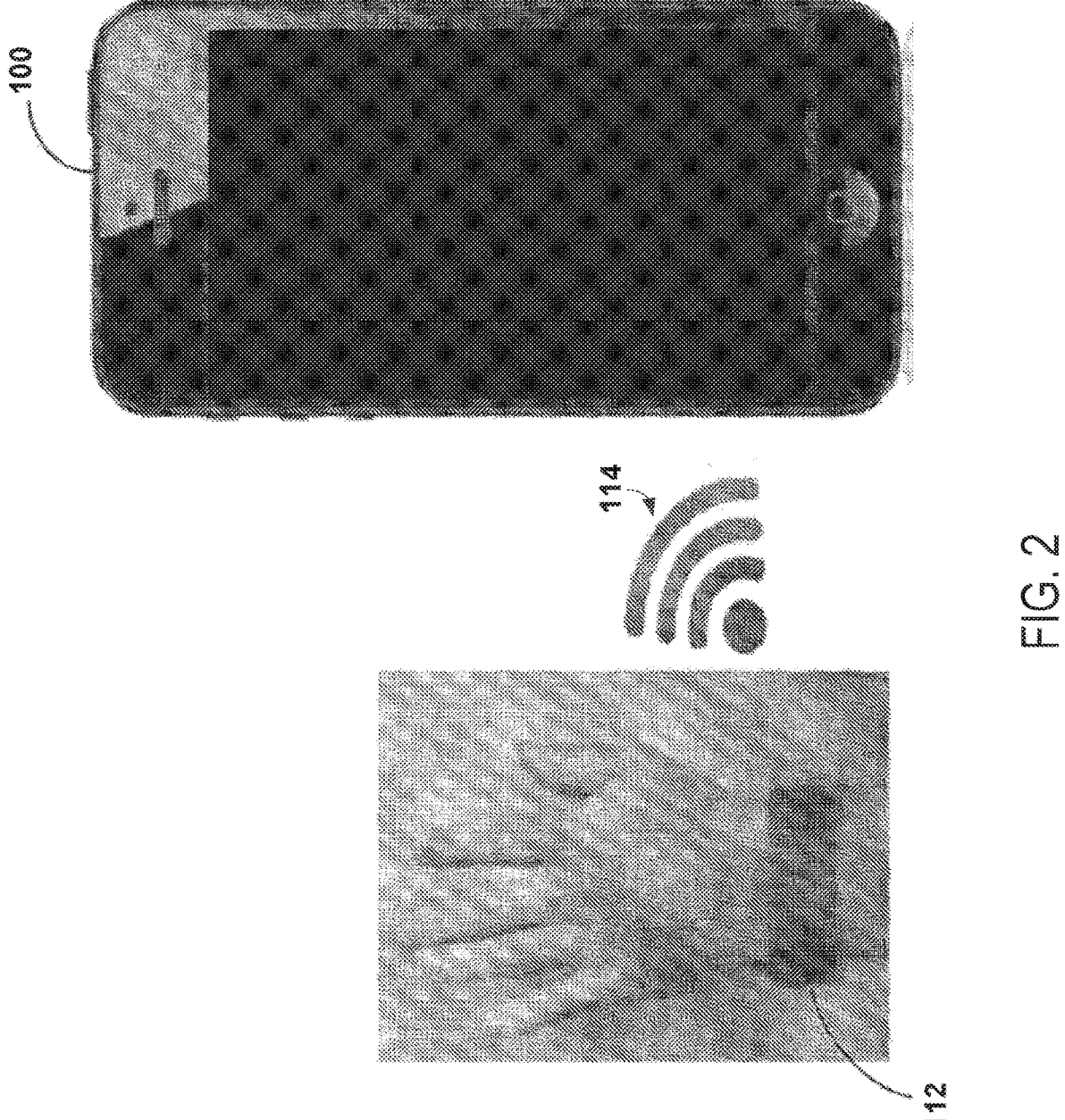
FIG. 2 depicts a computing device, including a wireless sensor that is communicatively coupled to the computing device, according to an example embodiment.

FIG. 2 depicts one embodiment of the computing device 100 and the sensor(s) 112. In FIG. 2, the sensor(s) 112 takes the form of a wearable wristband that is worn by a human subject and the computing device 100 takes the form of a mobile phone. The sensor(s) 112 may detect vibrations originating from a blood vessel at the subject's wrist and wirelessly transmit, via the connection mechanism 114 (e.g., via Bluetooth®), a signal representing the detected vibrations to the computing device 100. The computing device 100 may receive the signal for further processing as described further herein.

Figure 3:
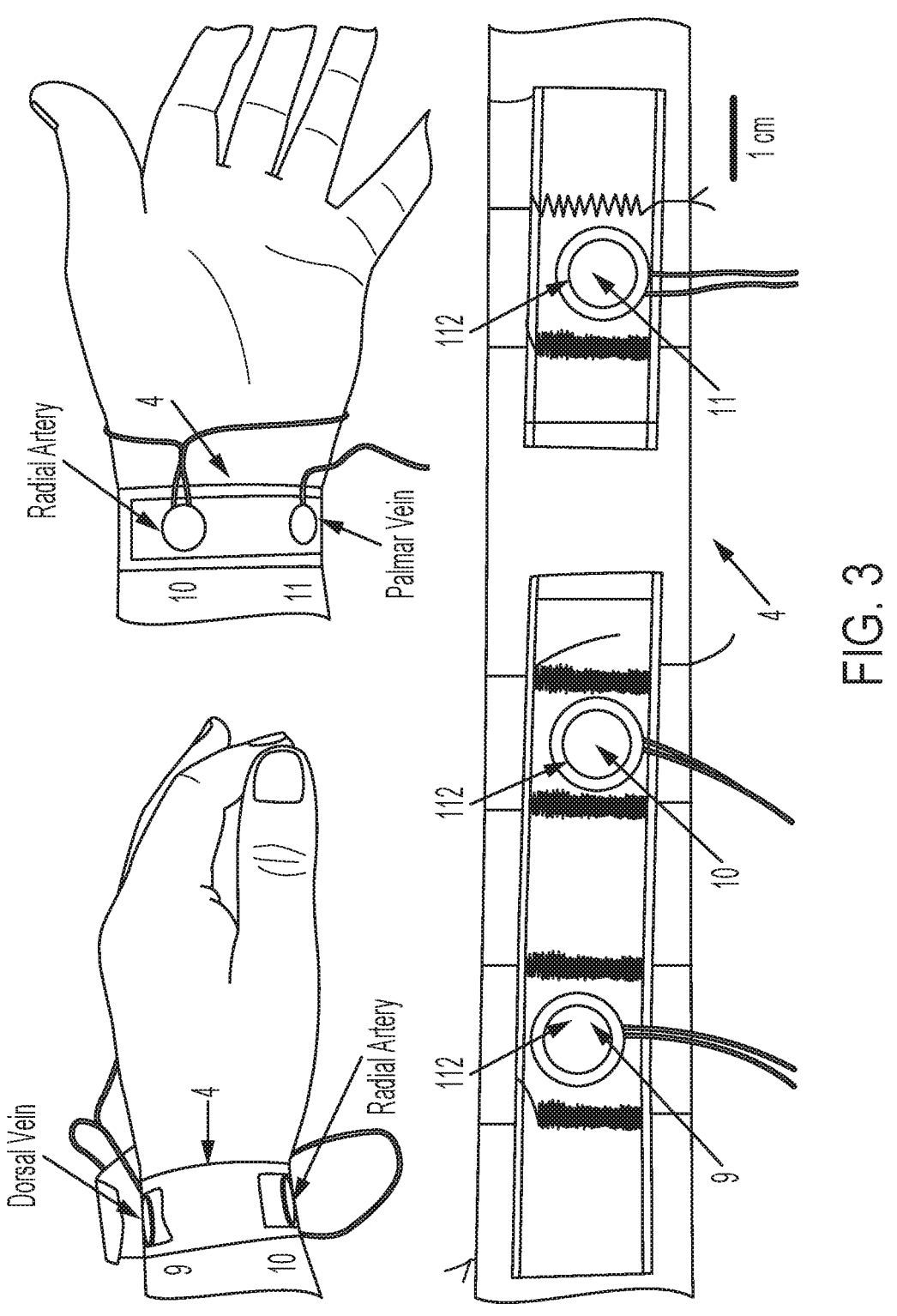
FIG. 3 includes photographs of a human wrist and hand and sensors for detection of blood vessel vibrations related to a subject's blood volume status and/or mechanical properties of the blood vessels, according to an example embodiment.

FIG. 3 depicts the sensor(s) 112 as being incorporated into a wrist band 4 that is worn on a human wrist. The sensor(s) 112 (e.g., piezoelectric sensors) are positioned respectively over the dorsal vein 9, the radial artery 10, and the palmar vein 11, and held in place by the tensioned wrist band 4.

FIG. 4 is a block diagram of a method 400 for determining a blood volume status of a subject.

At block 402, the method 400 includes generating, via a sensor of a computing device, a signal representing vibrations originating from a blood vessel of a subject. For example, the computing device 100, via the sensor(s) 112, may detect vibrations originating from a blood vessel (e.g., a vein wall or an artery wall) of a subject. The sensor(s) 112 can be positioned proximately to a peripheral vein or a peripheral artery of the subject to detect vibrations that originate from the peripheral vein or the peripheral artery.

The vibrations can be produced by fluid flowing through the blood vessel, can be produced by wall tension of the blood vessel, or can be produced by contraction or relaxation of the blood vessel in (e.g., physiological) response to the fluid flowing through the blood vessel. In a specific example, the sensor(s) 112 may be secured (e.g., via a Velcro strap) to the subject's skin above or near the blood vessel (see FIG. 3). The sensor(s) 112 may detect the vibrations caused by blood flow through the blood vessel as the vibrations are conducted through tissues such as the subject's skin.

The subject may be human, but other animals are possible. As the sensor(s) 112 detects the vibrations, the subject may be breathing spontaneously, e.g., without the aid of a mechanical ventilator, or with the aid of a mechanical ventilator.

At block 404, the method 400 includes decomposing the signal into one or more first intrinsic oscillatory modes and one or more second intrinsic oscillatory modes. In this context, the one or more first intrinsic oscillatory modes have respective oscillation frequencies that are less than respective oscillation frequencies of the one or more second intrinsic oscillatory modes.

Typically, the one or more first intrinsic oscillatory modes are useful for determining blood volume status of the subject or other subject related metrics, and the one or more second intrinsic oscillatory modes are useful for evaluating mechanical properties of the blood vessel or tissue adjacent to the blood vessel, as discussed below in the context of the method 500.

An intrinsic oscillatory mode of the signal can be defined as a mode (e.g., a component of the signal) having a number of extrema and a number of zero-crossings that are equal or that differ by no more than one. At any point in time, a mean value of an envelope defined by the local maxima of the mode and an envelope defined by the local minima of the mode will generally be zero. The envelopes will typically be defined by a cubic spline line that connects the local maxima and a cubic spline line that connects the local minima.

In some embodiments, decomposing the signal includes performing an empirical mode decomposition (e.g., a Hilbert-Huang transform (HHT)) or an ensemble empirical mode decomposition upon the signal to identify the one or more first intrinsic oscillatory modes and the one or more (e.g., three, four, or five) second intrinsic oscillatory modes. The one or more second intrinsic oscillatory modes are generally the highest order (e.g., highest frequency) intrinsic oscillatory modes of the signal.

The HHT is an iterative (e.g., sifting) process for identifying intrinsic oscillatory modes of the signal. First, all local minima and local maxima are identified in the time-domain signal generated at block 402. An upper envelope taking the form of a cubic spline line is generated to connect all of the local maxima of the signal, and a lower envelope taking the form of a cubic spline line is generated to connect all of the local minima of the signal. The time-dependent mean of the upper envelope and the lower envelope is then calculated and subtracted from the signal and the result is evaluated with respect to predetermined stoppage criteria (discussed in more detail below). If the result satisfies the stoppage criteria, the result is identified as the highest order intrinsic oscillatory mode (e.g., a first mode of the one or more second intrinsic oscillatory modes).

If the result of the first iteration of the process does not satisfy the stoppage criteria, another iteration of the process is performed. Another upper envelope taking the form of a cubic spline line can be generated to connect all of the local maxima of the result of the first iteration of the process, and a lower envelope taking the form of a cubic spline line can be generated to connect all of the local minima of the result of the first stage of the process. The time-dependent mean of the upper envelope and the lower envelope can then be subtracted from the result of the first iteration of the process and the result of the second iteration of the process can be evaluated with respect to the predetermined stoppage criteria. This process is repeated until the iterative result satisfies the stoppage criteria at which point a highest order intrinsic oscillatory mode has been identified.

Next, the identified intrinsic oscillatory mode can be subtracted from the signal generated at block 402 and the remaining portion of the signal is processed as described above to identify one or more additional intrinsic oscillatory modes.

In various embodiments, the computing device 100 determines a standard deviation of two consecutive iterative results of the sifting process and identifies the most recent result of the sifting process as an intrinsic oscillatory mode if the standard deviation is less than a threshold amount.

In other embodiments, the computing device 100 will continue the sifting process until the computing device 100 determines that for a threshold number of consecutive sifting processes the consecutive results have numbers of zero-crossings, local maxima, and local minima that are equal or at most differ by one. When these criteria are satisfied, the computing device 100 identifies the most recent result of the sifting process as an intrinsic oscillatory mode.

In other embodiments, the sifting process is continued until the most recent result is a monotonic function, in which case the result of the sifting process preceding the monotonic function is identified as an intrinsic oscillatory mode.

Due to the nature of the sifting process, the one or more second intrinsic oscillatory modes (e.g., higher frequency modes) are identified prior to the identification of the one or more first intrinsic oscillatory modes (e.g., lower frequency modes). In fact, the one or more second intrinsic oscillatory modes are generally used by the computing device 100 to further identify the one or more first intrinsic oscillatory modes.

At block 406, the method 400 includes obtaining an intensity spectrum of the one or more first intrinsic oscillatory modes over a range of frequencies (e.g., 0.05 Hz-25 Hz). More specifically, the computing device 100 may perform a Fourier transform (e.g., a fast Fourier transform (FFT)) upon the one or more first intrinsic oscillatory modes of the signal representing the lower frequency vibrations originating from the blood vessel. Frequencies of interest such as a subject's respiratory rate, a pulse rate, and harmonics or multiples of the pulse rate may take the form of "peaks" within the obtained intensity spectrum. Such peaks may take the form of local (or global) maxima of signal intensity with respect to signal frequency. The Fourier transform may be non-linear or linear and may additionally involve the performance of an autocorrelation function upon the one or more first intrinsic oscillatory modes.

At block 408, the method 400 includes using the obtained intensity spectrum to determine a blood volume status of the subject. In some embodiments, the computing device 100 can additionally or alternatively use the obtained intensity spectrum to determine subject metrics such as a pulmonary capillary wedge pressure (PCWP), a mean pulmonary arterial pressure, a pulmonary artery diastolic pressure, a left ventricular end diastolic pressure, a left ventricular end diastolic volume, a cardiac output, total blood volume, and a volume responsiveness of the subject.

In particular, the ratio of a peak corresponding to the subject's heart rate and a peak corresponding to a frequency that is double the subject's heart rate can be useful in determining blood volume status. For example, the computing device 100 can use the obtained intensity spectrum to generate a numerical score that represents the blood volume status or any of the subject metrics discussed above.

In some examples, the above methods can be performed both before and after treatment of the subject to determine the effectiveness of the treatment (e.g., to determine if fluid administration has altered the subject's blood volume to a more desirable level). For instance, the subject may be suffering from increased or decreased cardiac output compared to control, or increased or decreased intravascular volume status compared to control. Additionally or alternatively, the subject could be scheduled to undergo cardiac catheterization or have undergone cardiac catheterization to determine cardiac output or volume status. By further example, the subject could have or be under the effect of one or more of pneumonia, cardiac disorders, sepsis, asthma, obstructive sleep apnea, hypopnea, anesthesia, abnormal pain, or narcotic use.

In some examples, the computing device 100 can use the determined blood volume status or other determined metrics to determine an effect that administering a fluid to the subject would have on the subject (e.g., an increase, a decrease, or no change in cardiac output or blood volume status).

In some examples, the computing device 100 can use the determined blood volume status or other determined metrics to diagnose respiratory distress or hypoventilation in the subject.

In some embodiments, the computing device 100 can use the determined blood volume status or other determined metrics to provide, via the user interface 108, an indication of the determined blood volume status or other determined metrics. For example, the computing device 100 can determine that the determined blood volume status indicates hypovolemia or hypervolemia, and provide, via the user interface 108, an indication that the determined blood volume status indicates hypovolemia or hypervolemia in the subject.

In particular embodiments, the computing device 100 can adjust (e.g., in real time) a flow rate of fluid that is provided intravenously to the subject based on the determined blood volume status or other subject metrics.

In some embodiments, the computing device 100 uses the obtained intensity spectrum to determine a heart rate of the subject and provides, via the user interface 108, an indication of the determined heart rate.

In particular embodiments, the computing device 100 makes a determination, via an accelerometer (e.g., part of the sensors 112) of the computing device 100, that a current rate of movement of the subject is less than a threshold rate of movement. In response, the computing device 100 can perform the method 400 or the method 500 and/or related actions. This can help prevent the computing device 100 from performing processing operations during subject movement (e.g., exercise) that might erroneously alter determinations of various subject metrics.

Block 408 may involve using known statistical correlations between previously collected intensity spectra of subject blood vessel vibrations and the aforementioned subject metrics. For example, blood vessel vibration data may be collected for a number of subjects while one or more of the aforementioned metrics are directly measured for each of the subjects. This data may then be used to determine statistical correlations between the collected blood vessel vibration data and the aforementioned subject metric data. More specifically, such correlations between the blood vessel vibration data and the subject metric data can be approximated as mathematical functions using various statistical analysis or "curve fitting" techniques (e.g., least squares analysis). As such, future subject metrics may be determined indirectly (e.g., without direct measurement) and non-invasively with the sensor(s) 112 by performing the identified mathematical functions upon subsequently collected blood vessel vibration intensity data.

Any of the aforementioned subject metrics that are determined using the above methods may be used to diagnose or treat one or more of the following disorders: hypervolemia, hypovolemia, euvolemia, dehydration, heart failure, tissue hypoperfusion, myocardial infarction, hypotension, valvular heart disease, congenital heart disease, cardiomyopathy, pulmonary disease, arrhythmia, drug effects, hemorrhage, systemic inflammatory response syndrome, infectious disease, sepsis, electrolyte imbalance, acidosis, renal failure, hepatic failure, cerebral injury, thermal injury, cardiac tamponade, preeclampsia/eclampsia, or toxicity. The determined subject metrics may also be used to diagnose respiratory distress or hypoventilation due to one or more of the following conditions: pneumonia, cardiac disorders, sepsis, asthma, obstructive sleep apnea, hypopnea, anesthesia, pain, or narcotic use.

The method 400 and related functionality is described in more detail below with reference to FIGS. 6-23.

Figure 5:
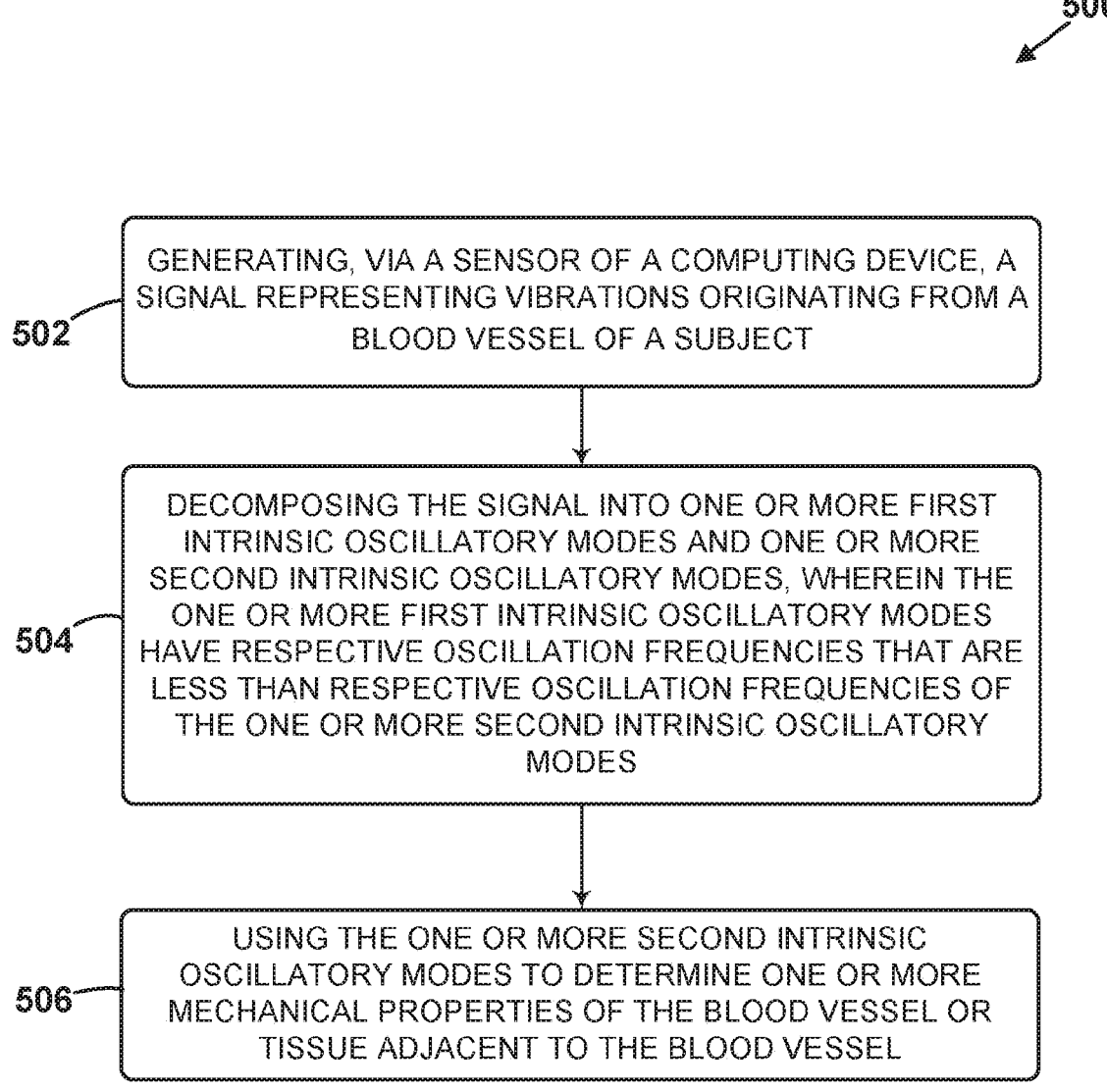
FIG. 5 is a block diagram of a method, according to an example embodiment.

FIG. 5 is a block diagram of a method 500 for determining one or more mechanical properties of a subject's blood vessel or tissue adjacent to the blood vessel.

At block 502, the method 500 includes generating, via a sensor of a computing device, a signal representing vibrations originating from a blood vessel of a subject. The computing device 100 can perform block 502 in any manner similar to block 402 described above.

At block 504, the method 500 includes decomposing the signal into one or more first intrinsic oscillatory modes and one or more second intrinsic oscillatory modes. In this context, the one or more first intrinsic oscillatory modes have respective oscillation frequencies that are less than respective oscillation frequencies of the one or more second intrinsic oscillatory modes.

Typically, the one or more first intrinsic oscillatory modes are useful for determining blood volume status of the subject or other subject related metrics, and the one or more second intrinsic oscillatory modes are useful for evaluating mechanical properties of the blood vessel or tissue adjacent to the blood vessel.

The computing device 100 can perform block 504 in any manner similar to block 404 described above.

At block 506, the method 500 includes using the one or more second intrinsic oscillatory modes (e.g., a dissipative shear waveform) to determine one or more mechanical properties of the blood vessel or tissue adjacent to the blood vessel.

In particular embodiments, the one or more second intrinsic oscillatory modes include one to three intrinsic oscillatory modes. In this context, the method 500 can further involve using the one to three (e.g., two) intrinsic oscillatory modes to determine whether the subject has edema. Additionally, the computing device 100 can display an indication of whether the subject has edema.

In some embodiments, using the one or more second intrinsic oscillatory modes to determine one or more mechanical properties of the blood vessel or tissue adjacent to the blood vessel includes generating and/or displaying a numerical score that represents the one or more mechanical properties.

In particular embodiments, using the one or more second intrinsic oscillatory modes to determine one or more mechanical properties of the blood vessel or tissue adjacent to the blood vessel includes determining a logarithmic decrement of the one or more second intrinsic oscillatory modes. The logarithmic decrement can be indicative of the mechanical properties as described below.

In some embodiments, using the one or more second intrinsic oscillatory modes to determine one or more mechanical properties of the blood vessel or tissue adjacent to the blood vessel includes determining a Q-factor of the one or more second intrinsic oscillatory modes. The Q-factor can be indicative of the mechanical properties as described below.

In particular embodiments, using the one or more second intrinsic oscillatory modes includes determining an anelastic coefficient of the one or more second intrinsic oscillatory modes.

In some examples, the method 500 is performed prior to carrying out a treatment of the subject and after carrying out the treatment to evaluate the treatment's effectiveness.

In particular embodiments, the user interface 108 provides an indication of the determined one or more mechanical properties of the blood vessel or adjacent tissue. As such, the one or more mechanical properties may indicate arteriosclerosis, edema, and/or elevated risk of aneurysm and the user interface 108 can provide an indication that the determined mechanical properties indicates arteriosclerosis, edema, and/or elevated risk of aneurysm.

In some examples, the method 500 involves determining a first amount of energy represented by the one or more first intrinsic oscillatory modes and a second amount of energy represented by the one or more second intrinsic oscillatory modes and using the determined first amount of energy and the determined second amount of energy to determine whether stiffening, plaque buildup, and/or other abnormal conditions are present in blood vessels of the subject.

The method 500 and related functionality is described in more detail below with reference to FIGS. 6-23.

Figure 6:
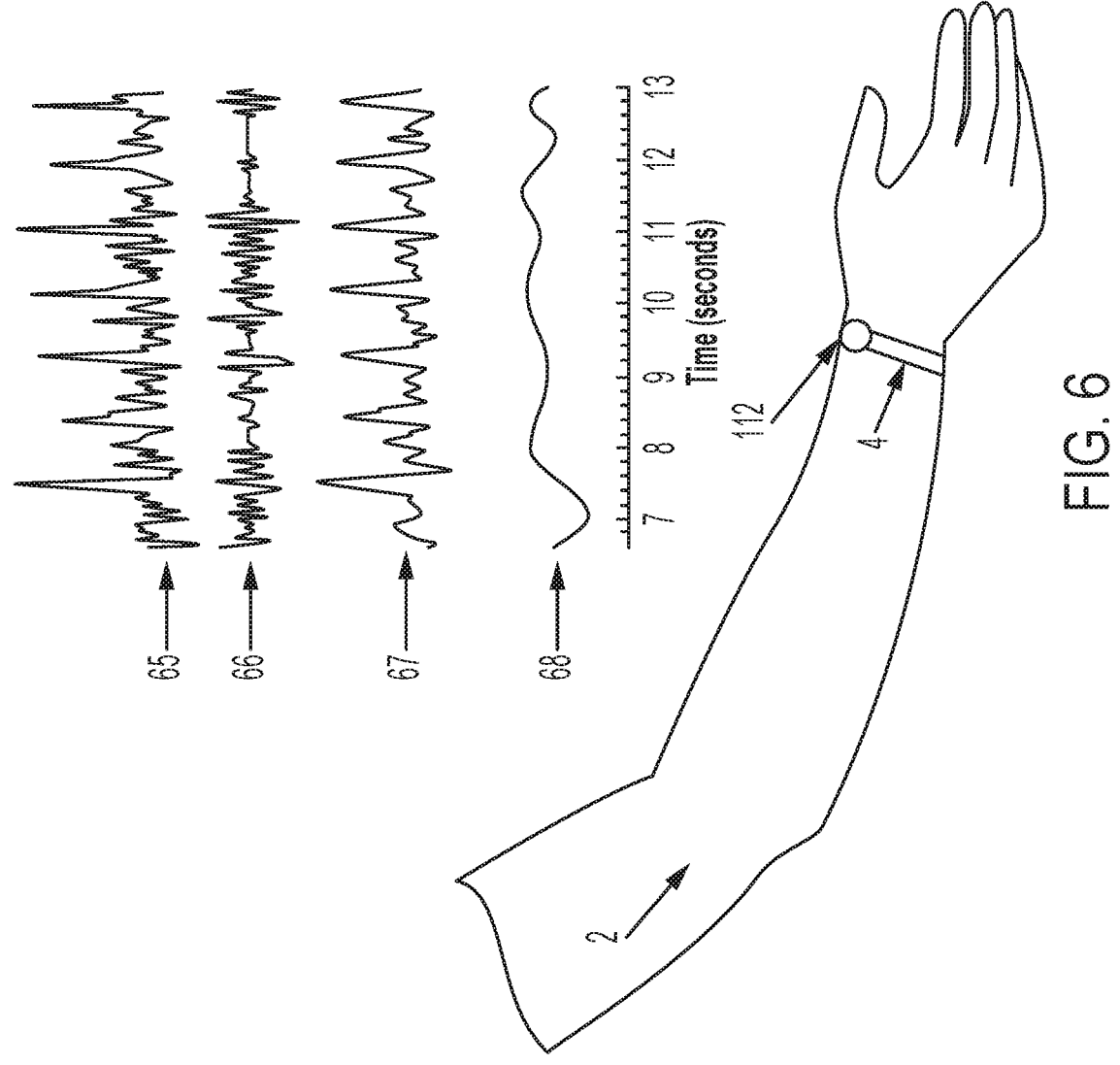
FIG. 6 includes an isometric view of an arm and graphical depictions of signals related to vibrations originating from a vein of a subject, according to an example embodiment.

FIG. 6 depicts an arm 2 of a human subject and waveforms 65, 66, 67, and 68 associated with methods disclosed herein. The sensor 112 is shown positioned over a vein of the subject, with the sensor 112 held in place by the wrist band 4. The waveforms 66, 67, and 68 can each represent an intrinsic oscillatory mode of the waveform 65 or a superposition of two or more intrinsic oscillatory modes of the waveform 65. The waveform 65 represents a full (e.g., undecomposed) signal detected by the sensor 112, also referred to herein as a peripheral venous waveform (PVW). The waveform 66 can be referred to herein as a high frequency dissipative shear waveform mode. The waveform 67 can be referred to herein as a venous pressure pulse waveform mode (e.g., the one or more first intrinsic oscillatory modes mentioned in the description of blocks 404 and 504 above). The waveform 68 can be referred to herein as a mean venous pressure waveform mode. Adding the three waveforms 66, 67 and 68 yields the original PVW denoted as waveform 65. Amplitude spectral density (ASD) analyses are conducted by the computing device 100 on the recomposed venous pressure pulse waveform mode waveform 67, and the amplitudes of the respective frequencies from the ASD correlate to the blood volume status of the subject as described further below.

Figure 7:
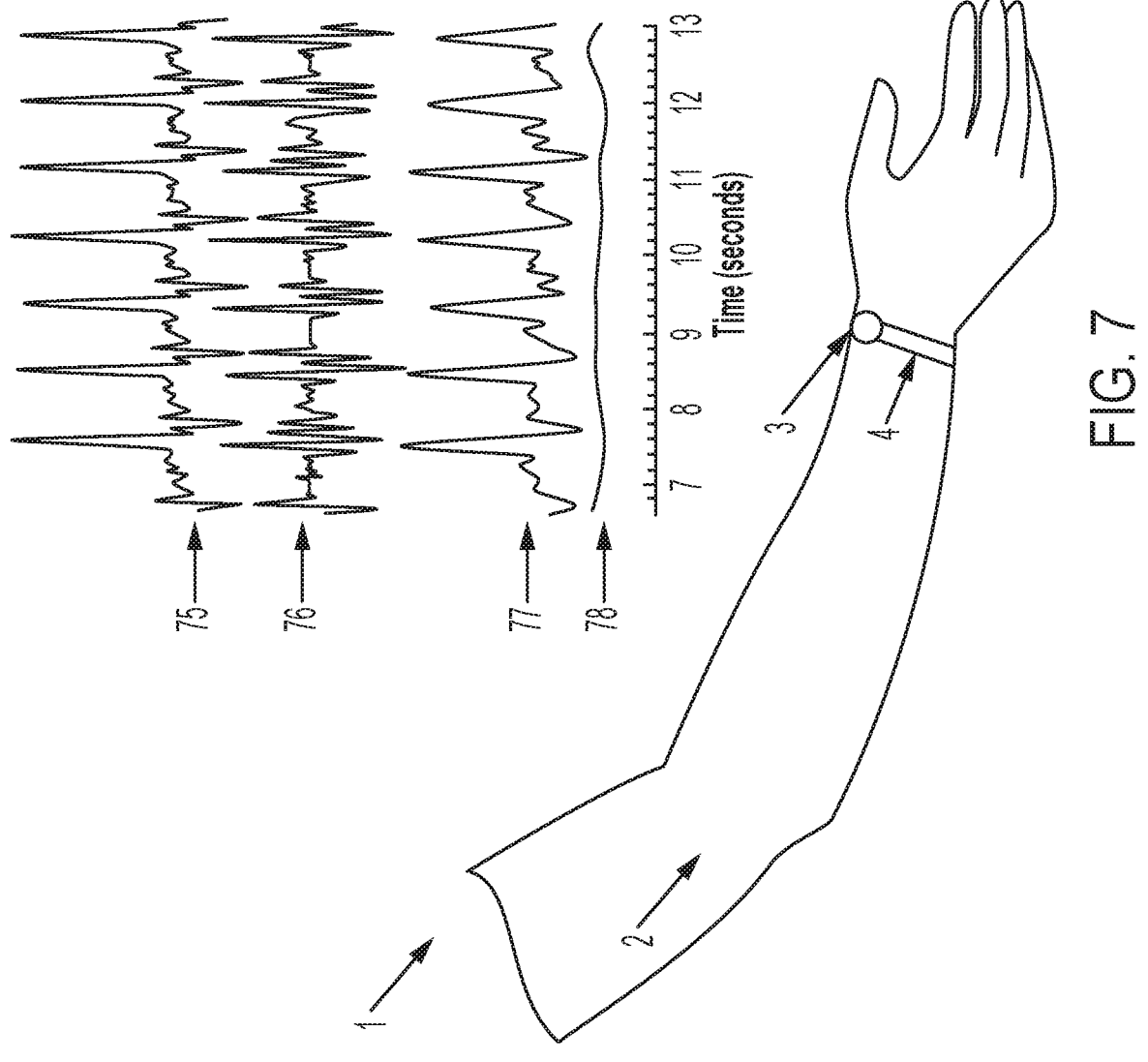
FIG. 7 includes an isometric view of an arm and graphical depictions of signals related to vibrations originating from an artery of the subject, according to an example embodiment.

FIG. 7 depicts an arm 2 of a human subject and waveforms 75, 76, 77, and 78 associated with methods disclosed herein. The sensor 112 is shown positioned over an artery of the subject, with the sensor 112 held in place by the wrist band 4. The waveforms 76, 77, and 78 can each represent an intrinsic oscillatory mode of the waveform 75 or a superposition of two or more intrinsic oscillatory modes of the waveform 75. The waveform 75 represents a full (e.g., undecomposed) signal detected by the sensor 112, also referred to herein as a peripheral arterial waveform (PAW). The waveform 76 can be referred to herein as a high frequency dissipative shear waveform mode. The waveform 77 can be referred to herein as an arterial pressure pulse waveform mode (e.g., the one or more first intrinsic oscillatory modes mentioned in the description of blocks 404 and 504 above). The waveform 78 can be referred to herein as a mean arterial pressure waveform mode. Adding the three waveforms 76, 77 and 78 yields the original PAW denoted as waveform 75. Amplitude spectral density (ASD) analyses are conducted by the computing device 100 on the recomposed arterial pressure pulse waveform mode waveform 77, and the amplitudes of the respective frequencies from the ASD correlate to the blood volume status of the subject as described further below.

Figure 8:
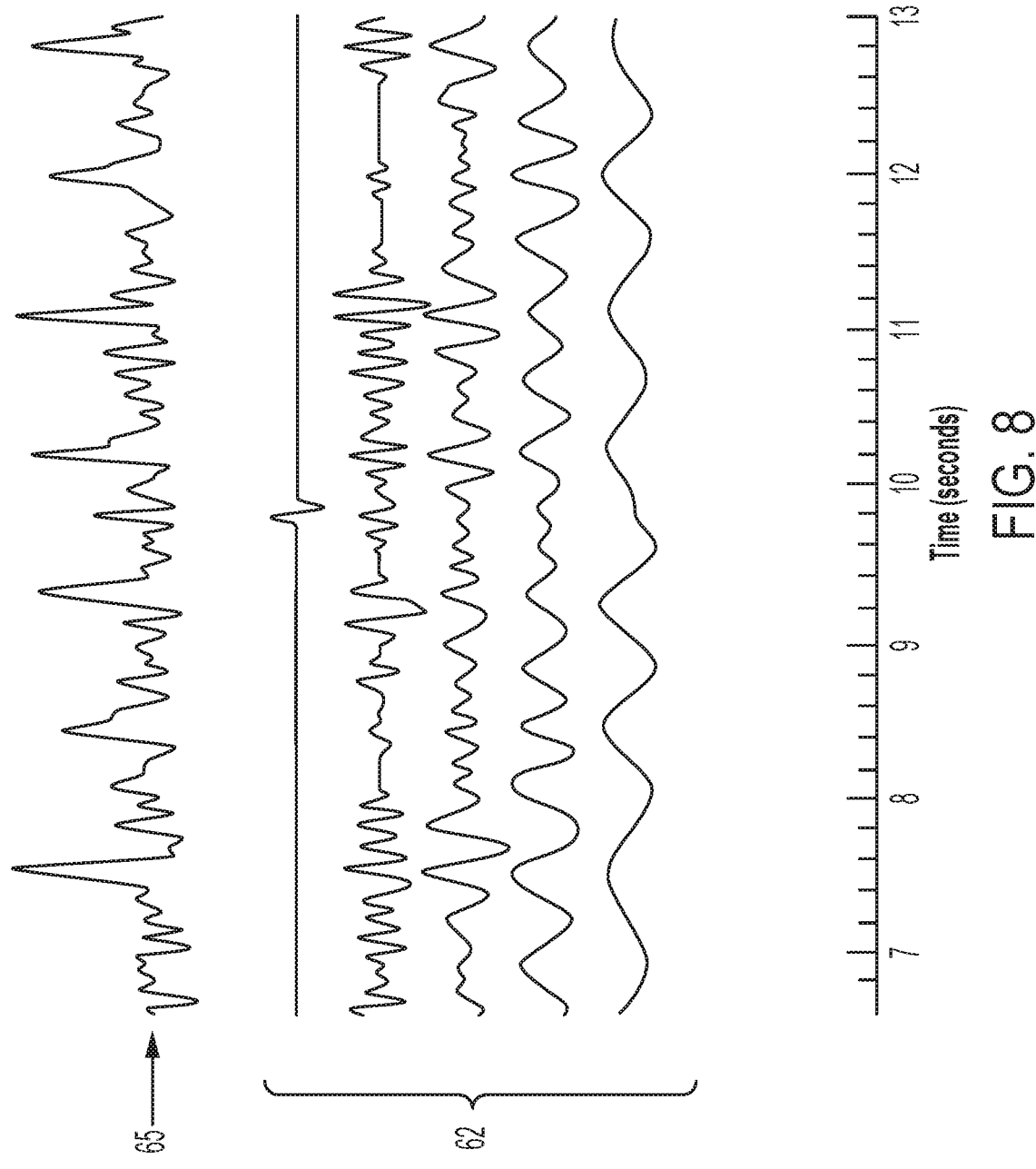
FIG. 8 includes graphical depictions of signals related to vibrations originating from a vein of the subject, according to an example embodiment.

FIG. 8 shows the time-dependent PVW waveform 65 which can be decomposed into its intrinsic oscillatory modes by the computing device 100. Some of the intrinsic oscillatory modes are shown collectively as waveforms 62. Typically, up to fourteen (14) intrinsic oscillatory modes can be isolated from the PVW waveform 65 using processes such as empirical mode decomposition (EMD), ensemble empirical mode decomposition (EEMD), and/or a Hilbert-Huang transform (HHT). The decomposition of the PVW waveform 65 into its intrinsic oscillatory modes generally begins with the shortest period oscillatory mode first being identified, that mode then being subtracted from the original PVW waveform 65, and the next shortest period oscillatory mode is found, and so on, until all the intrinsic oscillatory modes are determined as shown collectively (in part) as the waveforms 62. The sum of all of the intrinsic oscillatory modes yields the original PVW waveform 65. The intrinsic oscillatory modes are general in nature and can accommodate non-linear waveform analysis, and unlike constant amplitude and/or frequency in a simple harmonic component, the intrinsic oscillatory modes can have variable amplitude and frequency along the time axis.

Figure 9:
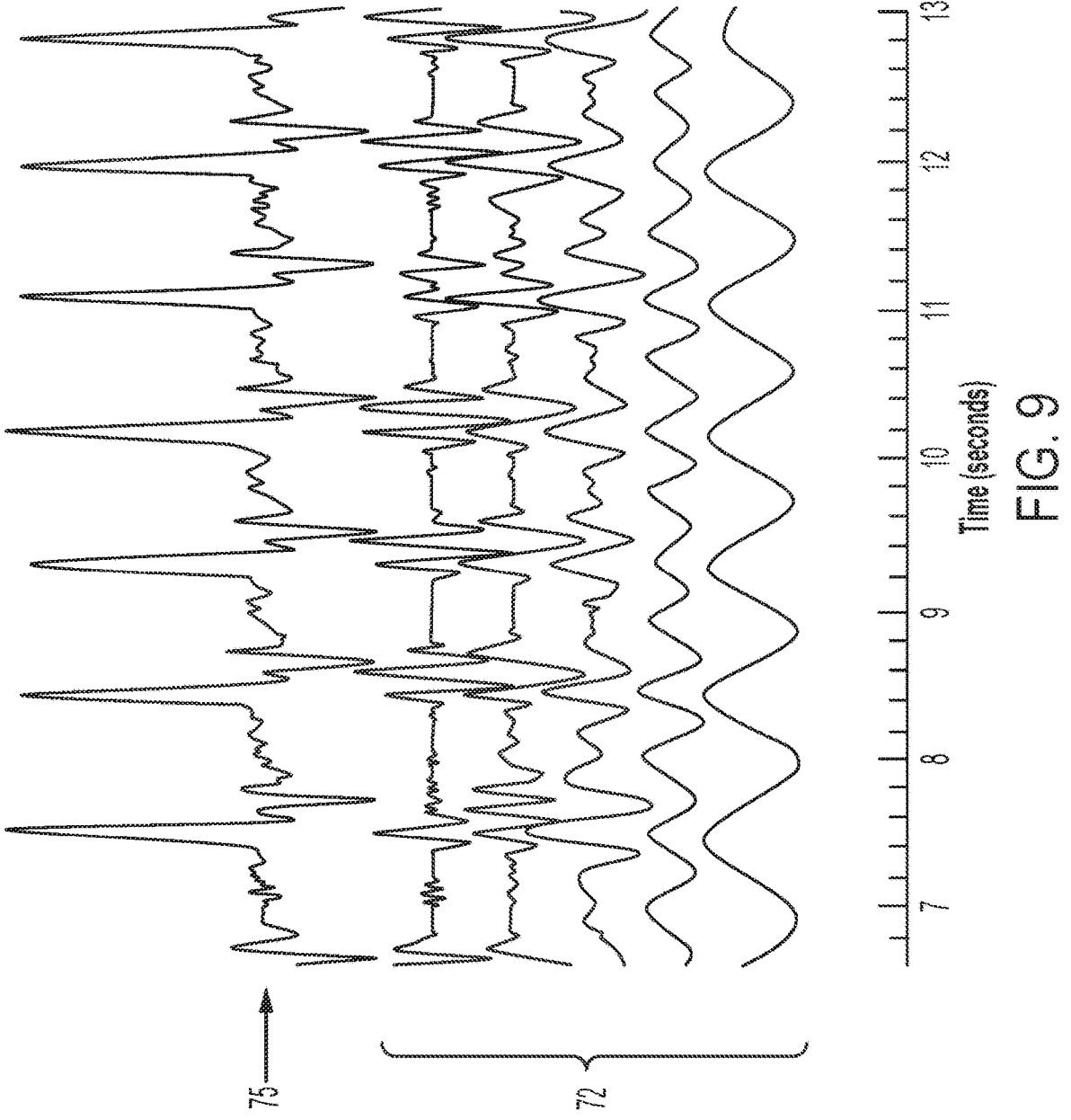
FIG. 9 includes graphical depictions of signals related to vibrations originating from an artery of the subject, according to an example embodiment.

FIG. 9 shows the time-dependent PAW waveform 75 which can be decomposed into its intrinsic oscillatory modes by the computing device 100. Some of the intrinsic oscillatory modes are shown collectively as waveforms 72. Typically, up to fourteen (14) intrinsic oscillatory modes can be isolated from the PAW waveform 75 using processes such as empirical mode decomposition (EMD), ensemble empirical mode decomposition (EEMD), and/or a Hilbert-Huang transform (HHT). The decomposition of the PAW waveform 75 into its intrinsic oscillatory modes generally begins with the shortest period oscillatory mode first being identified, that mode then being subtracted from the original PAW waveform 75, and the next shortest period oscillatory mode is found, and so on, until all the intrinsic oscillatory modes are determined as shown collectively (in part) as the waveforms 72. The sum of all of the intrinsic oscillatory modes yields the original PAW waveform 75. The intrinsic oscillatory modes are general in nature and can accommodate non-linear waveform analysis, and unlike constant amplitude and/or frequency in a simple harmonic component, the intrinsic oscillatory modes can have variable amplitude and frequency along the time axis.

Figure 10:
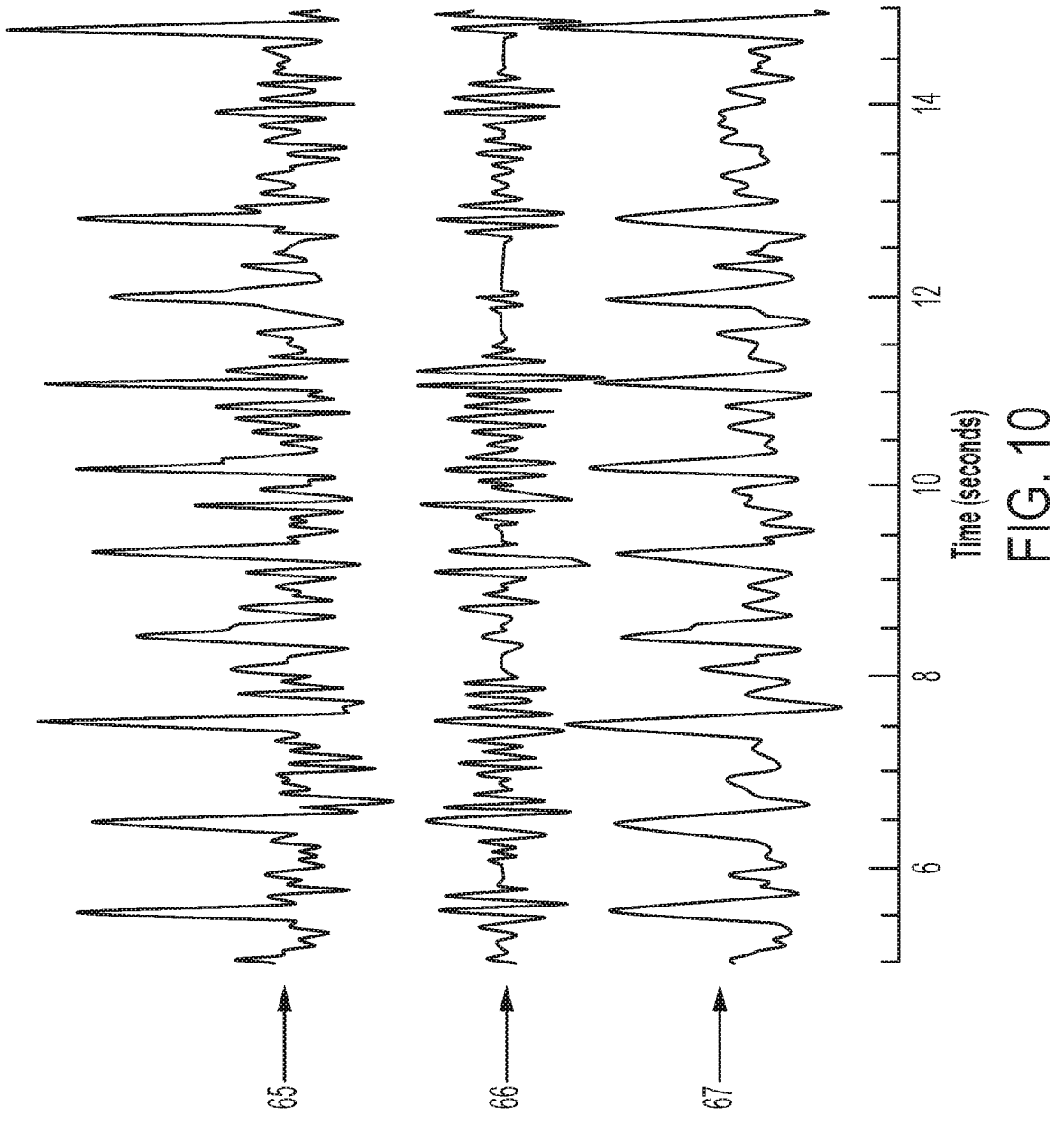
FIG. 10 includes graphical depictions of signals related to vibrations originating from a vein of the subject, according to an example embodiment.

FIG. 10 shows the PVW waveform 65, and the two recomposed waveforms 66 and 67 each representing a superposition of a plurality of intrinsic oscillatory modes of the PVW waveform 65. The waveform 66 can be referred to herein as the high frequency dissipative shear waveform mode, in some cases composed of the sum of first four (4) (e.g., highest frequency) intrinsic oscillatory modes. Thus, the waveform 66 can represent the one or more second intrinsic oscillatory modes referred to herein. The waveform 67 can be referred to herein as the venous pressure pulse waveform mode, being the sum of typically the next five (e.g., lower frequency) intrinsic oscillatory modes of the PVW. Thus, the waveform 67 can represent the one or more first intrinsic oscillatory modes referred to herein.

The number of the short period intrinsic modes that compose the waveform 66, depend on the sensor type, its housing and how it is incorporated into the wrist band strap, and its attachment to the subject. The number of modes composed in waveform 66 can be automatically calculated by the computing device 100 from a ASD analysis, since the sum of the intrinsic modes has energy predominantly in the second order heart rate frequency harmonic and higher harmonics. Typically, the first two (2) (e.g., highest frequency) intrinsic modes are of such low amplitude and high frequency as to be ignored in further analysis for healthy patients. However, for patients suffering from edema, high frequency pressure waves are excited and reflected by the propagating pressure pulse due to presence of fluids surrounding the venous blood vessels, and as such the edema state of the patient can be correlated to the energy composed in this intrinsic mode and in higher intrinsic modes. As depicted in FIG. 10, the computing device 100 can calculate and display (e.g., in real time) these recomposed waveforms 66 and 67, thus providing valuable insight into the characteristics of the subject.

The high frequency highly dissipative waveform mode 66 is typical of the high frequency shear waves that are generated by the propagating venous pressure pulse as a highly dissipative conical wake of high frequency shear waves. Typically, the next five intrinsic modes, the fifth, sixth, seventh and eighth modes, are summed to yield a venous pulse pressure waveform 67. The initiation, peak, and attenuation of the highly dissipative shear waveforms 66 can be seen to be correlated to the propagating venous pulse pressure waveform 67. The ratio of the energy in the waveform 66 compared to energy in the waveform 67 is typically ~60% for the palmar and dorsal veins respectively for a healthy subject, and values that deviate from these values indicate stiffening, biological aging, arteriosclerosis, disease and plaque buildup in the patient's blood vessels.

Figure 11:
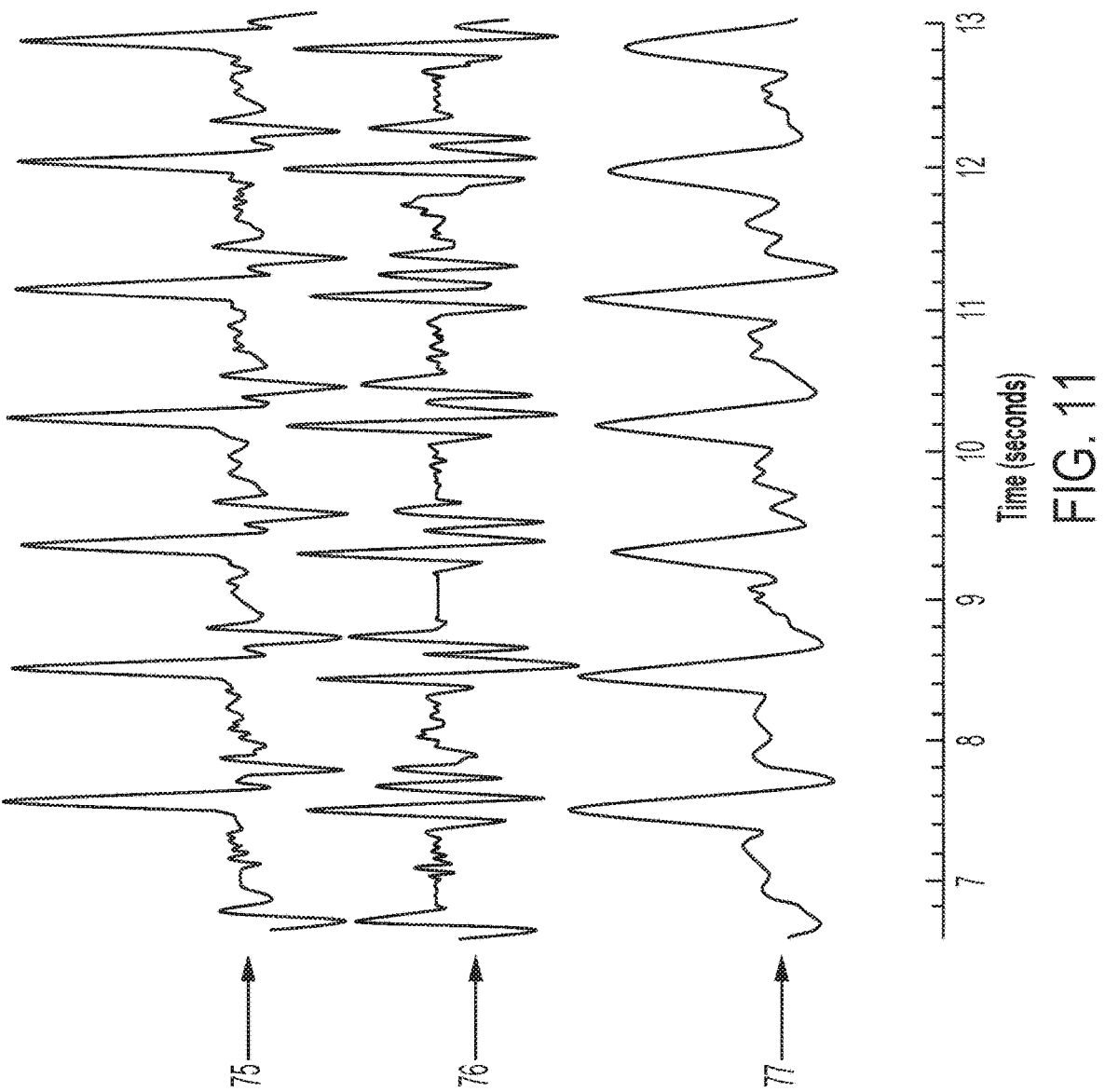
FIG. 11 includes graphical depictions of signals related to vibrations originating from an artery of the subject, according to an example embodiment.

FIG. 11 shows the PAW waveform 75, and the two recomposed waveforms 76 and 77 each representing a superposition of a plurality of intrinsic oscillatory modes of the PAW waveform 75. The waveform 76 can be referred to herein as the high frequency dissipative shear waveform mode, in some cases composed of the sum of first four (4) (e.g., highest frequency) intrinsic oscillatory modes. Thus, the waveform 76 can represent the one or more second intrinsic oscillatory modes referred to herein. The waveform 77 can be referred to herein as the arterial pressure pulse waveform mode, being the sum of typically the next five (e.g., lower frequency) intrinsic oscillatory modes of the PAW. Thus, the waveform 77 can represent the one or more first intrinsic oscillatory modes referred to herein. The number of the short period intrinsic modes that compose the waveform 76, depend on the sensor type, its housing and how it is incorporated into the wrist band strap, and its attachment to the subject. The number of modes composed in waveform 76 can be automatically calculated by the computing device 100 from a ASD analysis, since the sum of the intrinsic modes has energy predominantly in the second order heart rate frequency harmonic and higher harmonics. Typically, the first two (2) (e.g., highest frequency) intrinsic modes are of such low amplitude and high frequency as to be ignored in further analysis for healthy patients. However, for patients suffering from edema, high frequency pressure waves are excited and reflected by the propagating pressure pulse due to presence of fluids surrounding the arterial blood vessels, and as such the edema state of the patient can be correlated to the energy composed in this intrinsic mode and in higher intrinsic modes. As depicted in FIG. 11, the computing device 100 can calculate and display (e.g., in real time) these recomposed waveforms 76 and 77, thus providing valuable insight into the characteristics of the subject.

The high frequency highly dissipative waveform mode 76 is typical of the high frequency shear waves that are generated by the propagating arterial pressure pulse as a highly dissipative conical wake of high frequency shear waves. Typically, the next five intrinsic modes, the fifth, sixth, seventh and eighth modes, are summed to yield an arterial pulse pressure waveform 77. The initiation, peak, and attenuation of the highly dissipative shear waveforms 76 can be seen to be correlated to the propagating arterial pulse pressure waveform 77. The ratio of the energy of typically the two (2) highest frequency intrinsic modes (e.g., the waveform 76) to the energy contained in the waveform 77 quantify the degree of edema presence in the patient. The ratio of the energy in the waveform 76 compared to energy in the waveform 77 is typically ~60% for the arteries of a healthy subject, and values that deviate from these values indicate stiffening, biological aging, arteriosclerosis, disease and plaque buildup in the patient's blood vessels.

Figure 12:
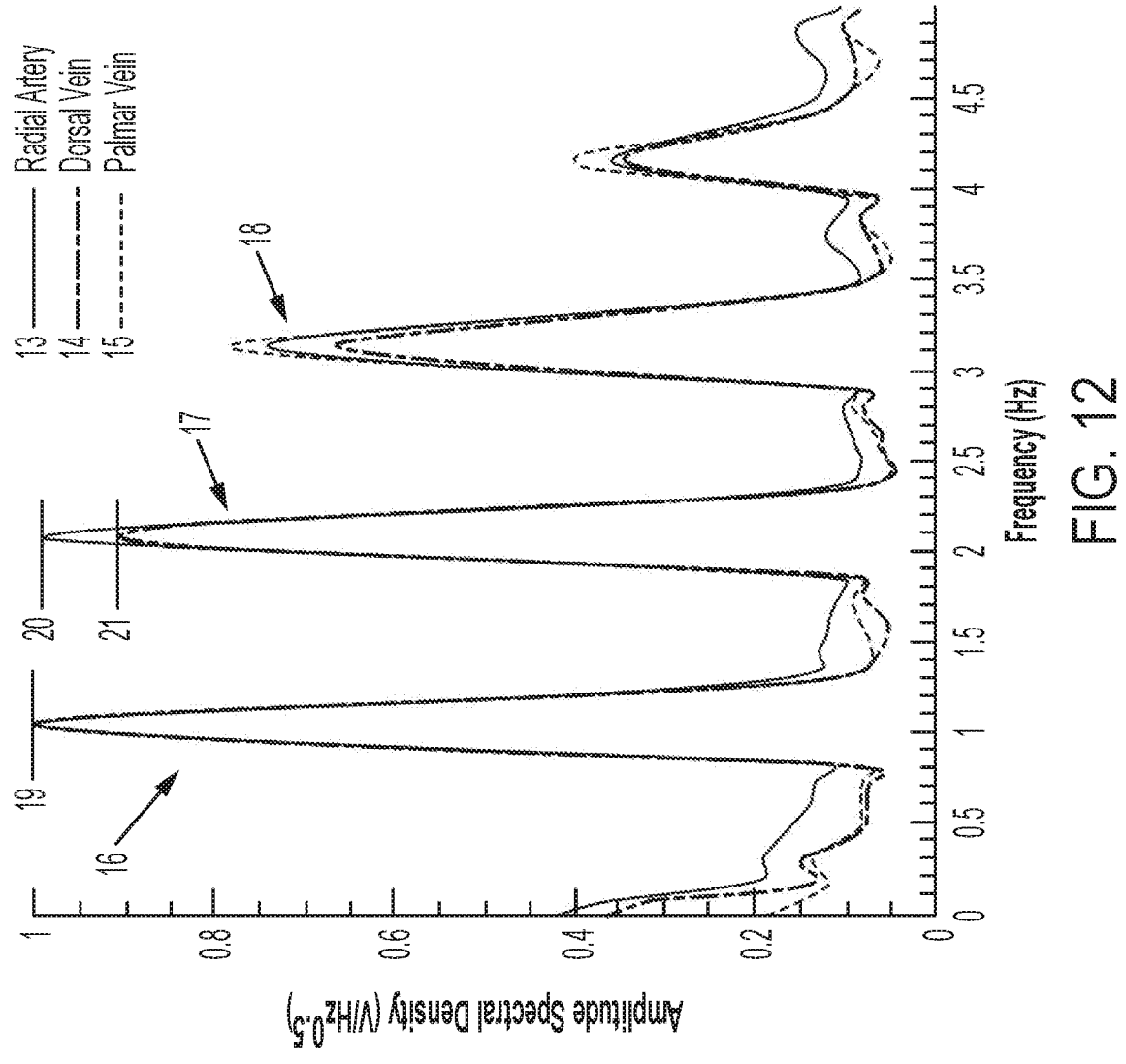
FIG. 12 is a graphical depiction of amplitude with respect to frequency of signals related to vibrations originating from blood vessels of the subject, according to an example embodiment.

FIG. 12 shows an amplitude spectral density (ASD) plot with respect to oscillation frequency of the waveforms 65 and 75 (see FIGS. 6 and 7) for a subject prior to exercise. In practice, the waveform 65 could correspond to the dorsal vein 14 or the palmar vein 15, and the waveform 75 could correspond to the radial artery 13. There are four (4) collections of prominent peaks in FIG. 12, namely peaks 16, 17, and 18, and a higher order collection of peaks that is not marked. Peak 16 corresponds to the heart rate of the subject, peak 17 corresponds to the first higher order harmonic (e.g., double the heart rate), and peak 18 corresponds to the second higher order harmonic (e.g., triple the heart rate), and so on. The respective amplitudes 19 of the peaks 16 have been mutually normalized for the radial artery 13, the dorsal vein 14, and the palmar vein 15. It is the ratio of the amplitudes of the peaks 17 to the peaks 16 that is generally of interest for determining blood volume status. In this data set, the ratio of the peak 17 to the peak 16 for the radial artery 13 is 1. The ratio of peak 17 to peak 16 for the dorsal vein 14 is 1. The ratio of peak 17 to peak 16 for the palmar vein 15 is 0.9.

Figure 13:
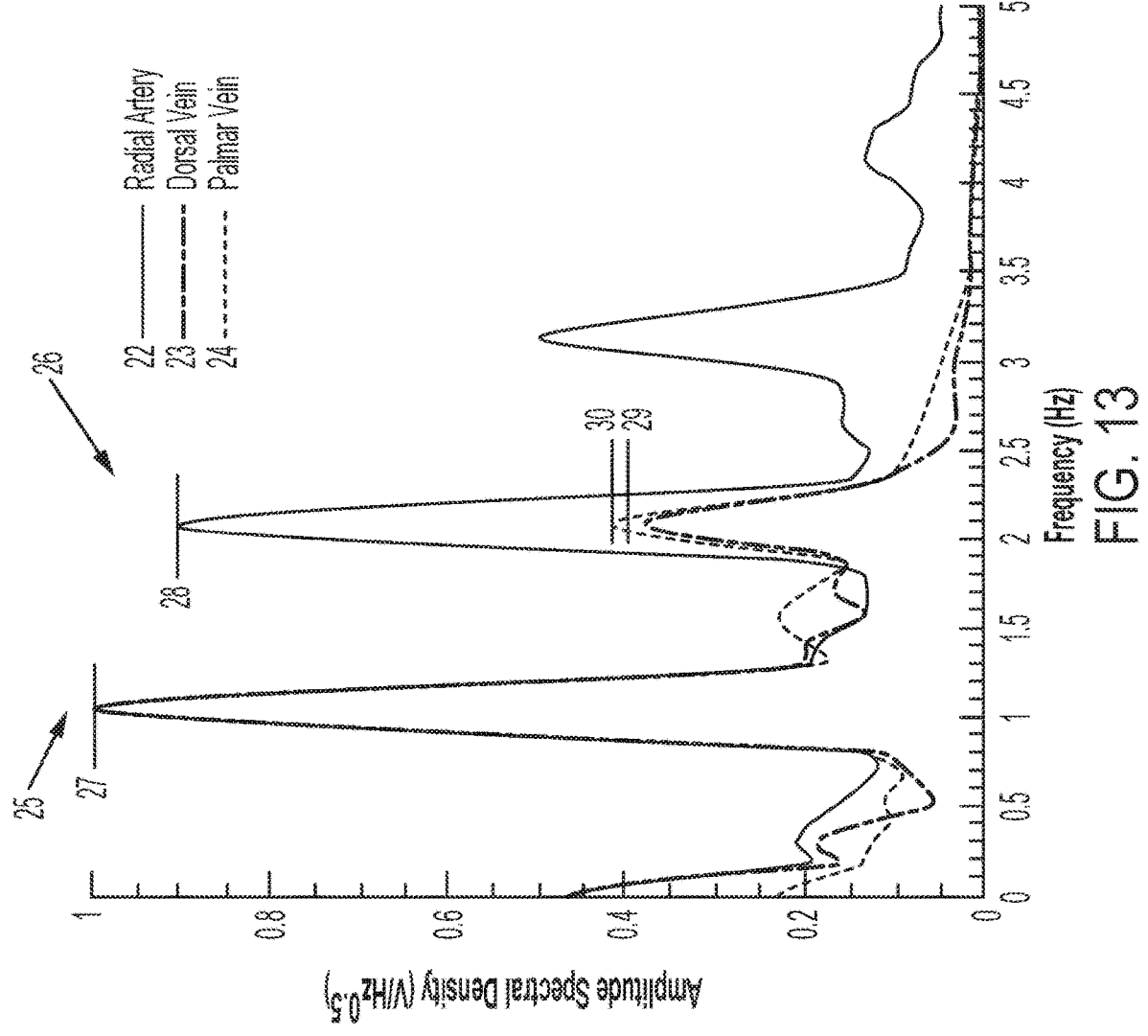
FIG. 13 is a graphical depiction of amplitude with respect to frequency of signals related to vibrations originating from blood vessels of the subject, according to an example embodiment.

FIG. 13 shows an amplitude spectral density (ASD) plot of the non-invasive indirect recomposed peripheral pressure pulse waveforms 67 and 77 (see FIGS. 6 and 7). The waveform 67 (e.g., the one or more first intrinsic oscillatory modes) typically represents a sum of the fifth, sixth, seventh and eighth intrinsic oscillatory modes of the PVW 65 prior to exercise for the dorsal vein 23 or the palmar vein 24. The waveform 77 (e.g., the one or more first intrinsic oscillatory modes) typically represents a sum of the fifth, sixth, seventh and eighth intrinsic oscillatory modes of the PAW 75 prior to exercise for the radial artery 22. There are two (2) distinct (marked) collections of peaks in FIG. 13. Peak 25 corresponds to the heart rate of the subject and peak 26 corresponds to the first higher order harmonic (e.g., double the heart rate). The amplitudes 27 of the peak 25 have been normalized for the artery and the two veins measured, and it is the ratio of the amplitudes of the peak 26 to the peak 25 that is generally of interest for determining blood volume status. As denoted for the two veins measured, after isolating the waveform 67, these amplitude ratios are now almost equal for the two veins 23 and 24, being about 0.4, while the amplitude ratio for the radial artery 22 (waveform 77) is 0.9.

Figure 14:
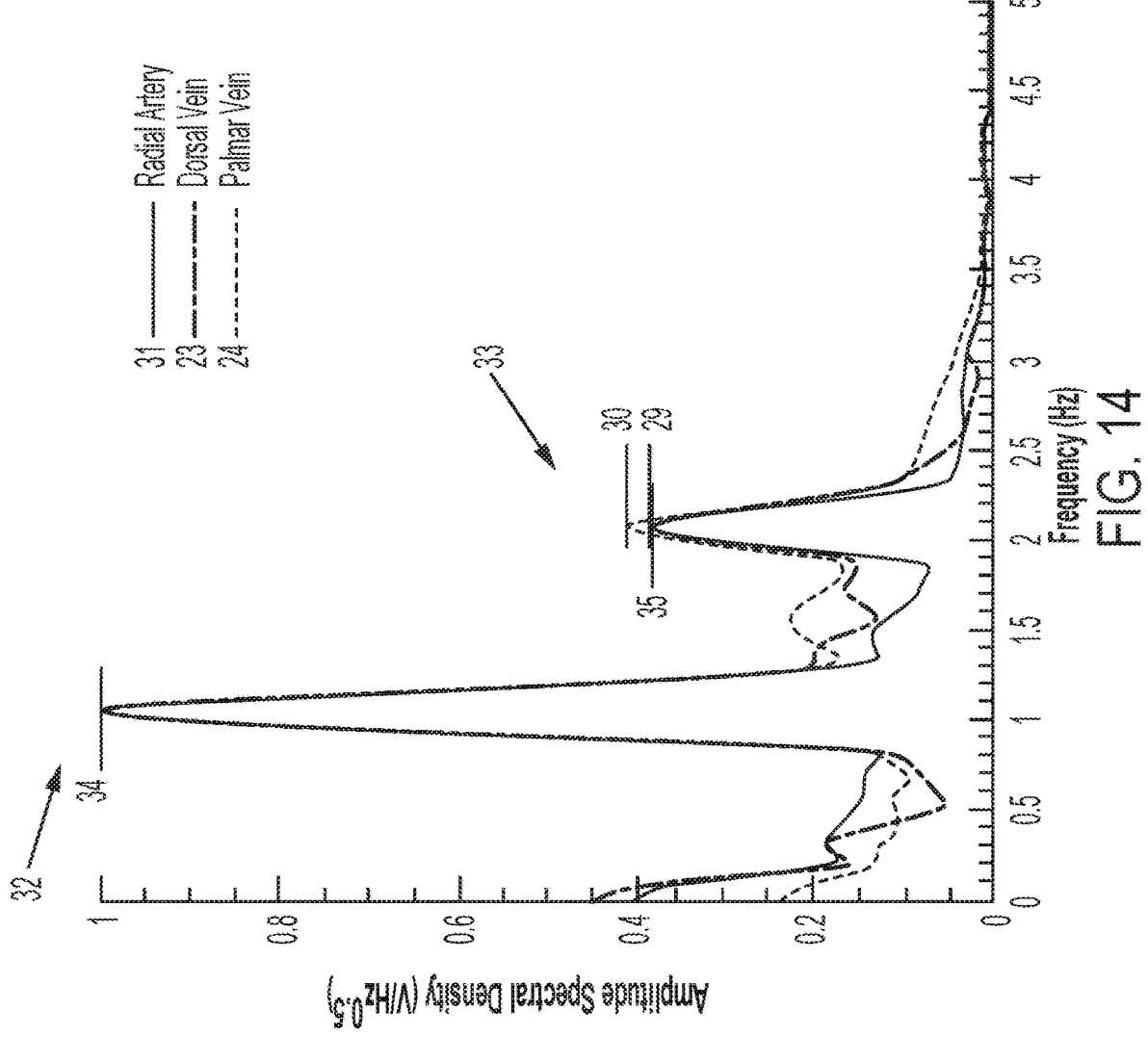
FIG. 14 is a graphical depiction of amplitude with respect to frequency of signals related to vibrations originating from blood vessels of the subject, according to an example embodiment.

FIG. 14 shows an amplitude spectral density (ASD) plot of the non-invasive indirect recomposed peripheral pressure pulse waveforms 67 (e.g., the one or more first intrinsic oscillatory modes) and 77 (e.g., the one or more first intrinsic oscillatory modes), being the sum of the last seven EEMD intrinsic oscillatory modes of the waveforms 65 and 75, respectively, for a patient prior to exercise, for the radial artery 31, the dorsal vein 23, and the palmar vein 24. There are two (2) distinct collections of peaks 32 and 33 in FIG. 14. Peak 32 corresponds to the subject's heart rate and peak 33 is its first higher order harmonic (e.g., double the heart rate). The amplitudes 34 of the peak 32, have been mutually normalized for the artery and the two veins measured, and it is the ratio of the amplitudes of the peak 33 to the peak 32 that is generally of interest for determining the blood volume status of the patient. These amplitude ratios are now almost equal for the artery and the two veins, being about 0.4.

Figure 15:
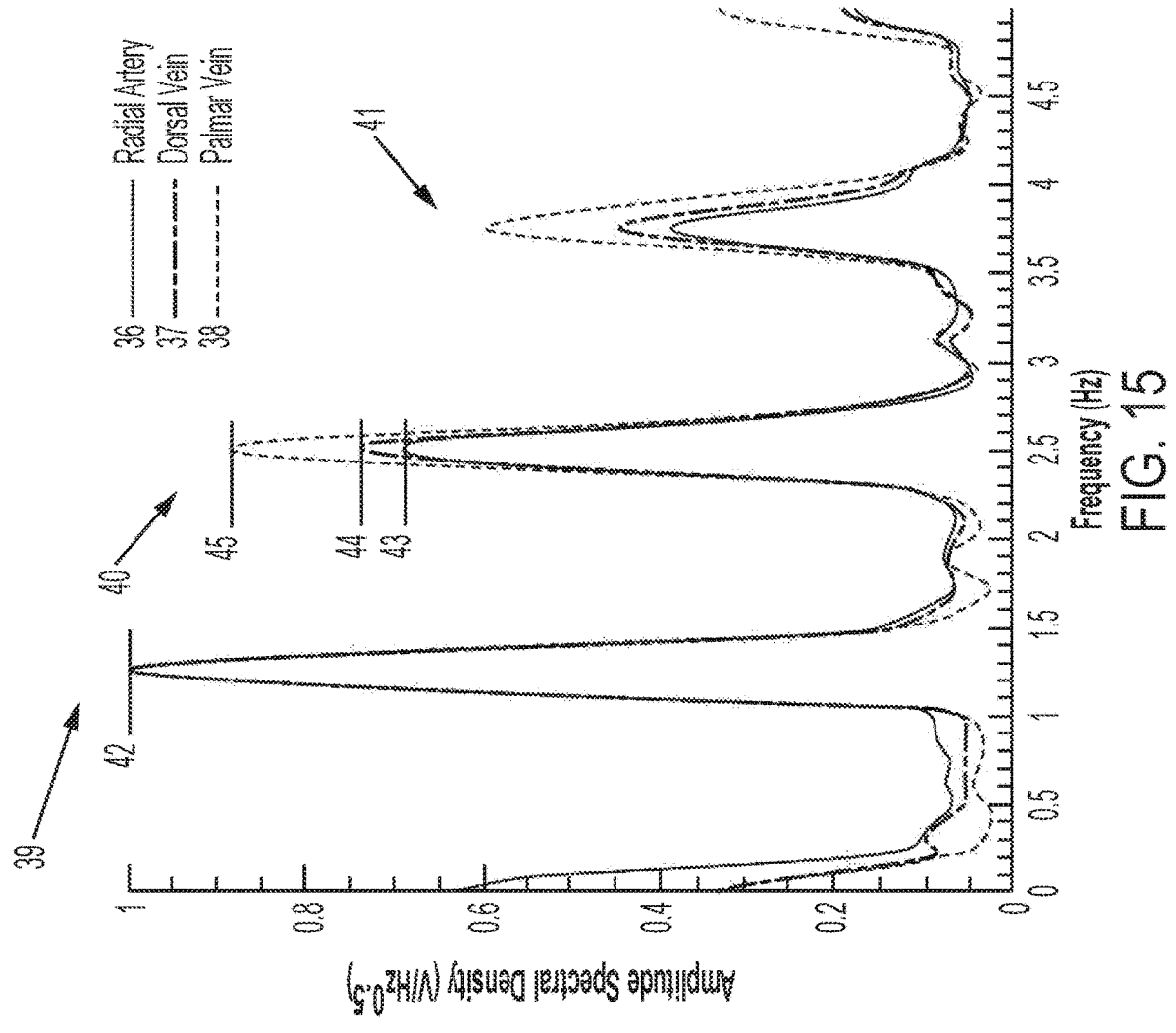
FIG. 15 is a graphical depiction of amplitude with respect to frequency of signals related to vibrations originating from blood vessels of the subject, according to an example embodiment.

FIG. 15 shows an amplitude spectral density (ASD) plot of the non-invasive indirect peripheral pressure pulse waveforms 67 (e.g., the one or more first intrinsic oscillatory modes) and 77 (e.g., the one or more first intrinsic oscillatory modes) for a subject following exercise and a loss of blood fluids, for the radial artery 36, the dorsal vein 37, and the palmar vein 38. There are three (3) distinct collections of peaks 39, 40, and 41 in FIG. 15. Peak 39 corresponds to the subject's heart rate, peak 40 corresponds to the first higher order harmonic (e.g., double the heart rate), and peak 41 corresponds to the second higher order harmonic (e.g., triple the heart rate), and so on. The amplitudes 42 of the peak 39 have been normalized for the artery and two veins measured, and it is the ratio of the amplitudes of the peak 40 to the peak 39 that is generally of interest for determining the blood volume status of the subject. These amplitude ratios are not equal for the two veins measured, being 0.7 and 0.9 for the dorsal vein 37 and the palmar vein 38 respectively, while the amplitude ratio for the radial artery is about 0.67.

Figure 16:
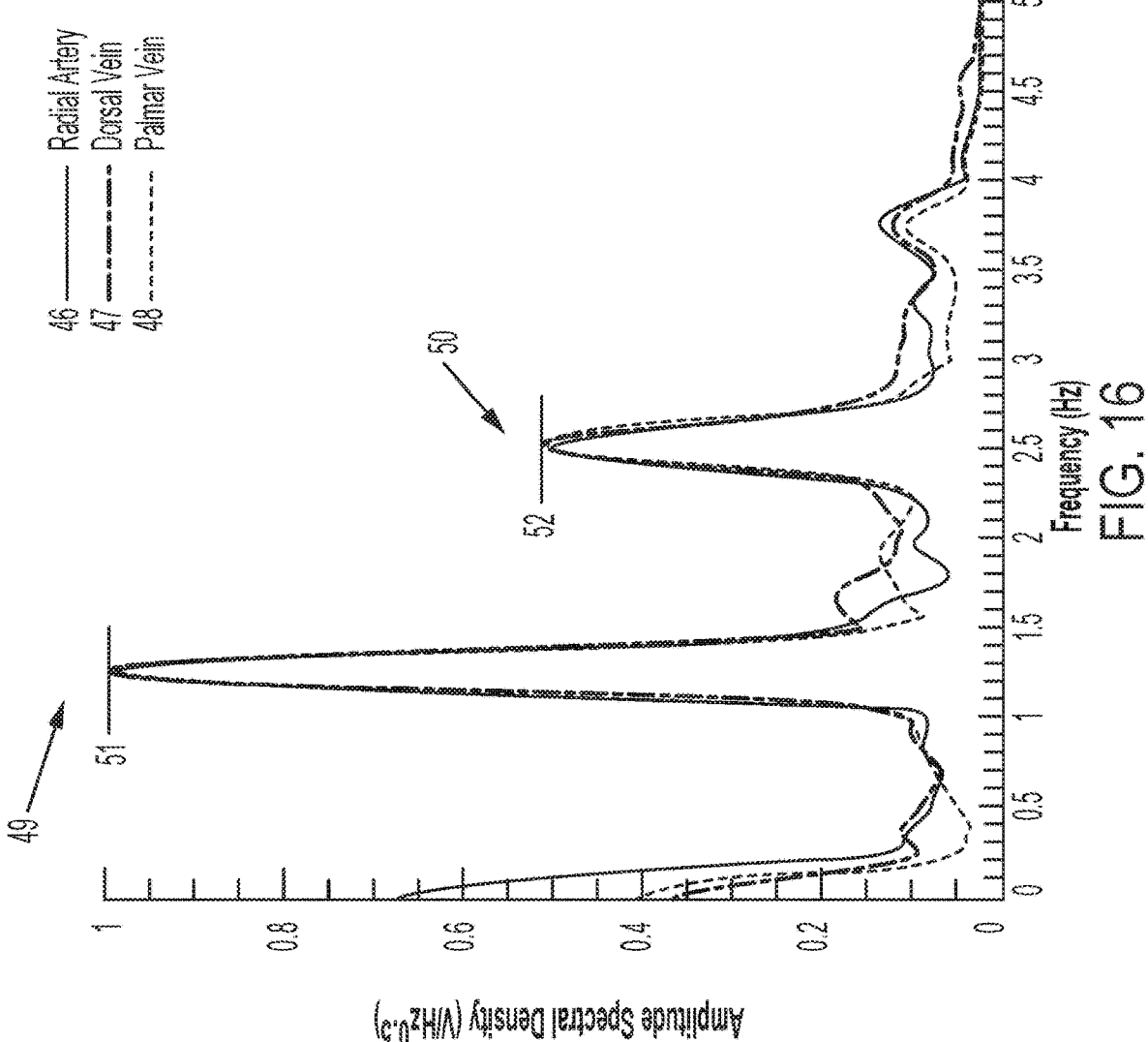
FIG. 16 is a graphical depiction of amplitude with respect to frequency of signals related to vibrations originating from blood vessels of the subject, according to an example embodiment.

FIG. 16 shows an amplitude spectral density (ASD) plot of the non-invasive indirect peripheral pressure pulse waveforms 67 (e.g., the one or more first intrinsic oscillatory modes) and 77 (e.g., the one or more first intrinsic oscillatory modes), being the sum of the fifth, sixth, seventh and eighth EMD intrinsic oscillatory modes of the waveforms 65 and 75, respectively for a patient following exercise and a loss of blood fluids, for the radial artery 46, for the dorsal vein 47, and the palmar vein 48. There are two (2) distinct (marked) collections of peaks in FIG. 16. Peak 49 corresponds to the subject's heart rate and peak 50 corresponds to the first higher order harmonic (e.g., double the heart rate). The amplitudes 51 of the peak 49 have been mutually normalized for the artery and the two veins measured, and it is the ratio of the amplitudes 52 of the peak 50 to the amplitudes 51 of the peak 49 that is generally of interest for determining the blood volume status of the subject. These amplitude ratios are equal for the artery and the two veins, being 0.5. The subject data shown in FIG. 16 is for a state of a loss of blood fluids, compared to the same subject prior to exercise, as shown in FIG. 14. The ratio of the amplitude peaks of the second to the first harmonics represent an absolute measure of the patient blood volume state, with the amplitude ratio rising from 0.4 to 0.5, upon the patient experiencing a loss of blood fluids, and this amplitude ratio is a direct representation of the subject's blood volume status.

The patient in FIG. 16 has just completely mild exercise, and as such their augmentation index is zero, since the body has adjusted the arterial vessels' compliance to be matched during exercise, and thus the arterial waves do not have any reflected "backward" traveling waves. In this state, the amplitude ratio as determined by EMD for the subject are the same for measurements over an artery or a vein, and represents an absolute value of the subject's blood volume status. The data represented by FIG. 14 was collected prior to exercise, and as such the subject's augmentation index was high, and thus the arterial waves have reflected "backward" traveling waves, and in this state, the amplitude ratio was determined by EEMD for the patient PAW.

This data confirms that the pulse waveform in both arteries and veins takes the form of a soliton, since encoded data in the pulse is maintained as the pulse travels from the heart, through the arteries and onward to the veins. The subject was evaluated prior to exercise, and thus had a high augmentation index, and thus reflected "backward" traveling waves are present in the arteries, and is the reason for the difference between the amplitude ratios of the artery compared to the veins, using the EMD method. In this case, the amplitude ratio from the venous data represents an absolute value of the subject's blood volume status. To remove the reflected "backward" traveling wave from the artery represented in FIG. 13 typically requires a non-linear procedure since the superposition of two (2) solitons is not linear. Due to the close proximity of reflectors in the artery, such as junction, termination, etc., the PAW becomes more complex especially from the reflected "backward" traveling wave. In this case, EMD tends to mode mix the intrinsic oscillatory modes, and therefore EEMD replaces EMD for the mode decomposition of the PAW, as shown in FIG. 14, with the amplitude ratios shown being equal for both the artery and the veins as a value of 0.4, representing the subject's blood volume status.

Figure 17:
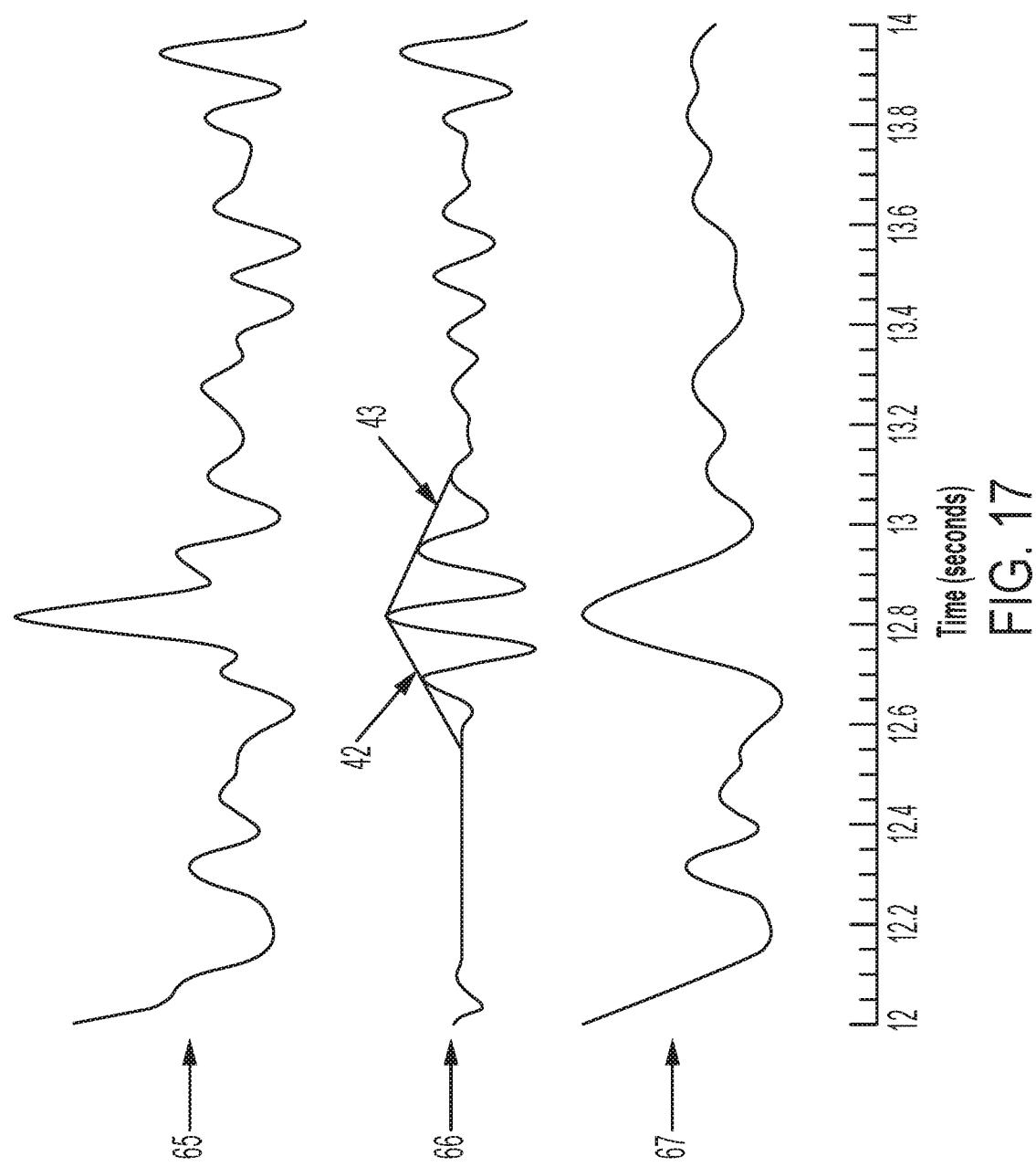
FIG. 17 includes graphical depictions of signals related to vibrations originating from a vein of the subject, according to an example embodiment.

FIG. 17 shows the PVW waveform 65, the venous pressure pulse waveform mode 67, and the high frequency highly dissipative shear waveform (venous) mode 66 (e.g., the one or more second intrinsic oscillatory modes). The high frequency highly dissipative waveform mode 66 is typical of the high frequency shear waves that are generated by the propagating venous pressure pulse as a highly dissipative conical wake of high frequency shear waves. The initiation, peak, and attenuation of the highly dissipative shear waveforms 66 can be seen to be correlated with the propagating venous pulse pressure waveform 67. The high frequency highly dissipative waveform mode 66 is initiated and generated by the propagating venous pressure pulse waveform 67 as a conical wake as shown by viewing the superimposed time histories of 66 and 67 as depicted. The rise form of 66 denoted as 42 is dependent on the pulse waveform 67, its propagating velocity and the properties of the blood and venous blood vessels. The attenuation or decay of 66 as denoted by 43 is dependent on the material properties of the venous blood vessels. The attenuation or decay can be computed via the logarithm decrement and the period of oscillation to yield the natural frequency and damping coefficient of the venous blood vessels walls in the vicinity of the intravenous line inserted in the subject. This data can be used to assess the state of the subject's venous blood vessels and also quantify over time any change in the state of the subject's fistulas used for dialysis treatment.

$$Q = \frac{\sqrt{4\pi^2 + \delta^2}}{4\delta} \qquad (1)$$

In equation (1), "Q" represents a quality factor and δ is the logarithmic decrement of the waveform 66. The logarithmic decrement δ denoted by 43 of the waveform 66 is typically about 0.36 for a healthy patient, yielding a quality factor of about Q≈4.37. Healthy arterial blood vessels have a quality factor of about Q≈3 and healthy venous blood vessels have a quality factor of about Q≈4.37. Q values greater than these values quantify the lack of anelasticity of the blood vessels, due to biological aging, arteriosclerosis, and/or disease. In the case of arteries, a Q>3 leads to increased circumferential tensile stresses at the artery inner wall due to the artery pressure pulse, and can lead to higher likelihood of aneurysms. The ratio of 1/Q is the normalized energy lost due to anelasticity of the blood vessel, during a complete load/unload (pressurize/depressurize) cycle as the pressure pulse travels along the blood vessel.

Figure 18:
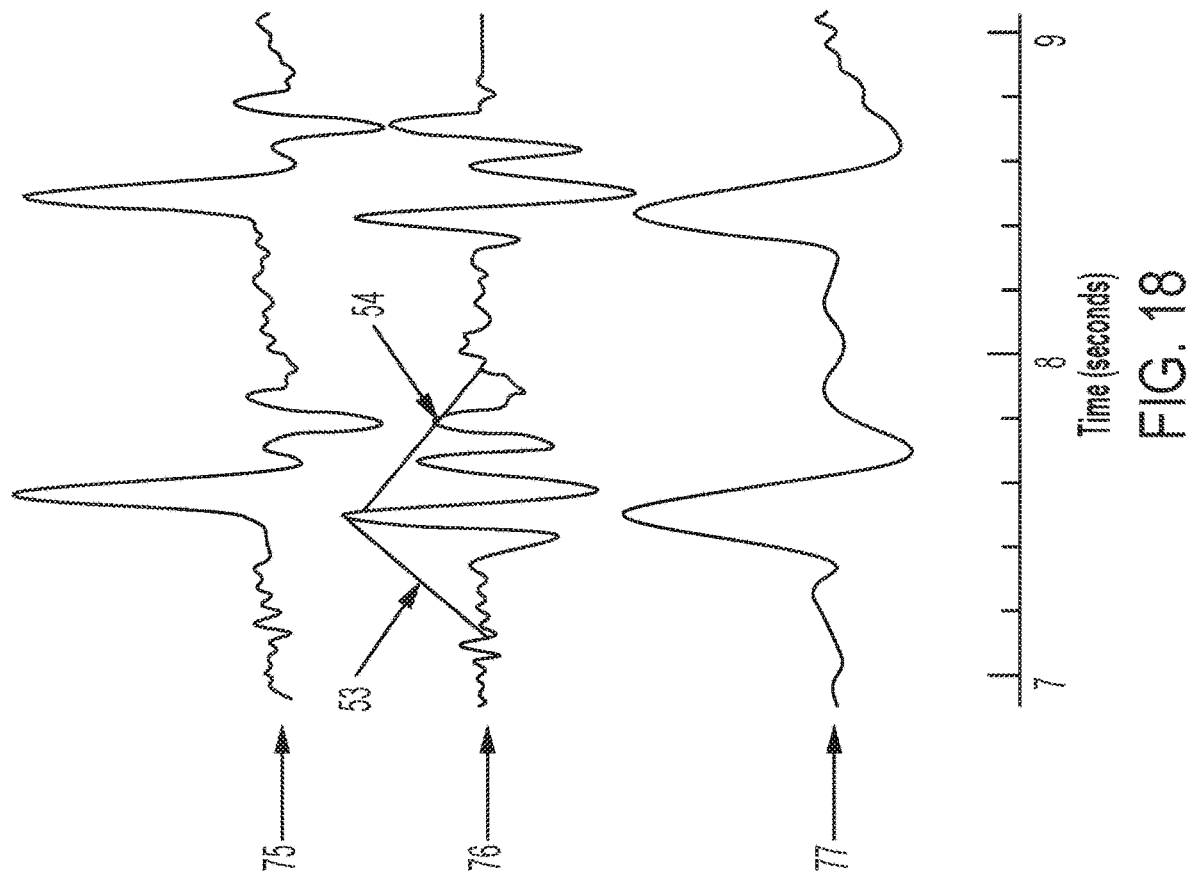
FIG. 18 includes graphical depictions of signals related to vibrations originating from an artery of the subject, according to an example embodiment.

FIG. 18 shows the PAW waveform 75, the arterial pressure pulse waveform mode 77, and the high frequency highly dissipative shear waveform (arterial) mode 76. The high frequency highly dissipative waveform mode 76 is typical of the high frequency shear waves that are generated by the propagating arterial pressure pulse as a highly dissipative conical wake of high frequency shear waves. The initiation, peak and attenuation of the highly dissipative shear waveform 76 can be seen to be correlated to the propagating arterial pulse pressure waveform 77. The high frequency highly dissipative waveform mode 76 is initiated and generated by the propagating arterial pressure pulse waveform 77 as a conical wake as shown by viewing the superimposed time histories of 76 and 77 as depicted. The rise form of 76 denoted as 53 is dependent on the pulse waveform of 77, its propagating velocity and the properties of the blood and arterial blood vessels. The attenuation or decay of 76 as denoted by 54 is dependent on the material properties of the arterial blood vessels. The attenuation or decay can be computed via the logarithm decrement and the period of oscillation to yield the natural frequency and damping coefficient of the arterial blood vessels walls in the vicinity of the intravenous line inserted in the patient. These data can assess the state of the patient's arterial blood vessels and also quantify over time any change in the state of a patient's fistulas used for dialysis treatment.

Figure 19:
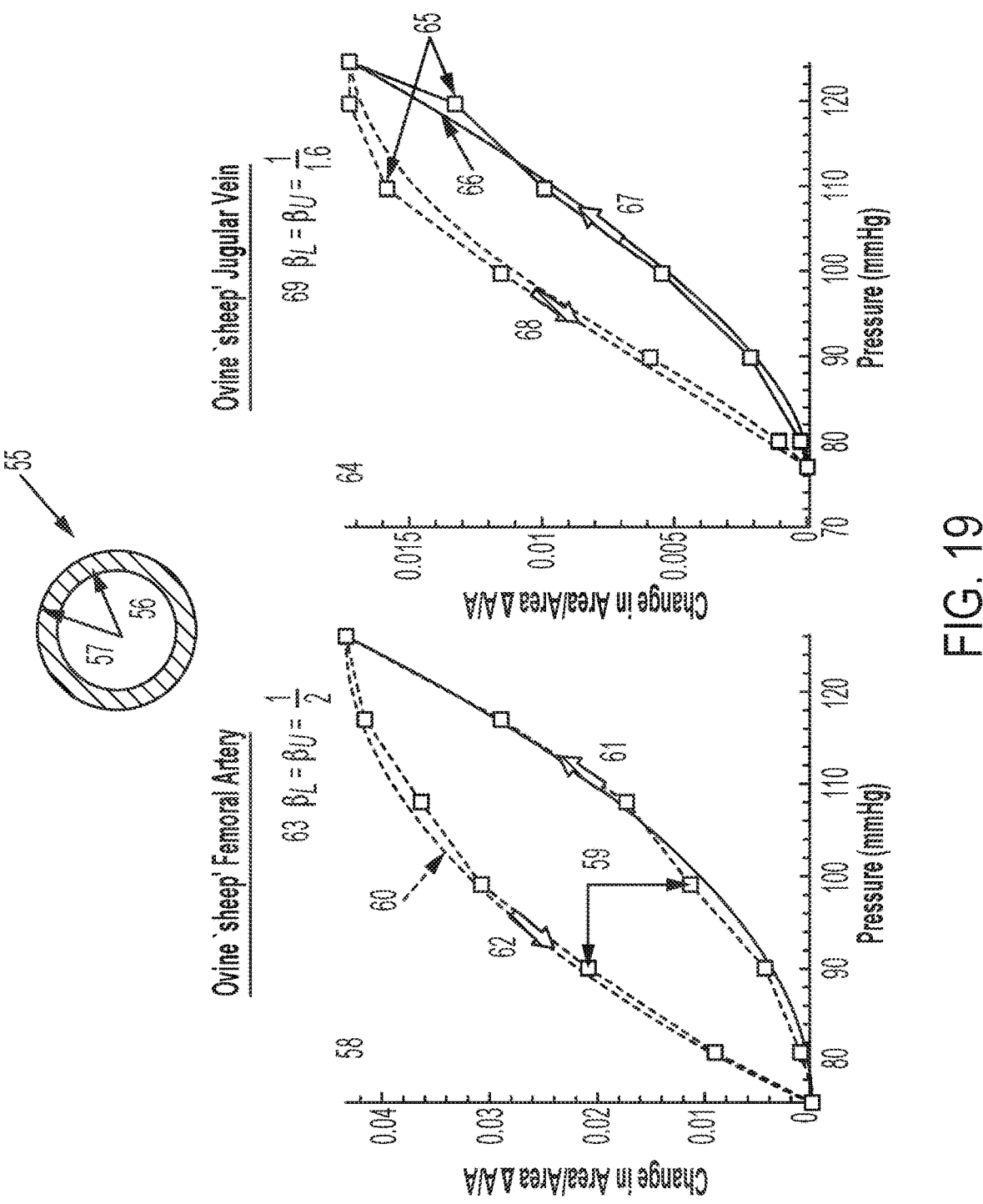
FIG. 19 is a pulse pressure plot versus change in area of a Ovine artery and a Ovine vein in vitro, and the thick wall anelastic power model fit for both the artery and vein under both loading (pressurizing) and unloading (depressurizing) pulse pressure, for the quantification of the patient's anelastic properties of the arterial blood vessels in the body, according to an example embodiment.

FIG. 19 shows a thick wall anelastic power model 55 of a blood vessel, with an inner wall radius 56 and an outer wall radius 57. FIG. 19 also shows a pulse pressure plot versus change in area of an Ovine artery 58, with the artery in vitro pressure area plot data 59, and the thick wall anelastic power model fit 60, for both the loading (pressurizing) 61 and unloading (depressurizing) 62 pulse pressure paths, with loading and unloading anelastic power law model fit shown as 63. FIG. 19 also shows the pulse pressure plot versus change in area of an Ovine vein 64, with the vein in vitro pressure versus area plot data 65, and the thick wall anelastic power model fit 66, for both the loading (pressurizing) 67 and unloading (depressurizing) 68 pulse pressure paths, with the anelastic power law model fit shown as 69. The anelastic thick wall power law model is given as:

$$\frac{\Delta A}{A} = \alpha \Delta p^\beta \qquad (2)$$

Where ΔA is the change in incremental cross-section area, A is the original cross-section area, α is a stiffness coefficient, Δp is the incremental pulse pressure above diastolic, and β is the power law coefficient, that can be different for the loading (pressurizing) path, as $\beta_L$, and $\beta_U$ for the unloading (depressurizing) path.

The power law coefficients that best fit the Ovine artery in vitro data in FIG. 19 are the same for the loading and unloading paths. That is, $\beta_L = \beta_U$, having a value of about 0.5 for a healthy artery. The importance of healthy anelastic arterial power law coefficients on a subject's state of health can be quantified from the thick wall anelastic power model as given by:

$$\sigma_\theta = -\Delta p \left( \frac{\left(\frac{a}{b}\right)^{2\beta}}{1 - \left(\frac{a}{b}\right)^{2\beta}} \right) + \frac{\Delta p(1 - 2\beta)}{\left(1 - (a/b)^{2\beta}\right)} \left(\frac{a}{r}\right)^{2\beta} \qquad (3)$$

Where $\sigma_\theta$ is the circumferential wall stress at a radius of r, "a" is the inner wall radius, and "b" is the outer wall radius, with Ge denoted as a tensile stress for negative values. From equation (3), and assuming an artery power law coefficient of exactly 0.5, the circumferential wall stress is a constant throughout the wall thickness, i.e. the inner wall tensile circumferential stress is equal to outer wall circumferential stress, and is the optimum case to minimize the inner wall circumferential tensile stress to be a minimum for a positive pulse pressure.

The Quality factor (Q) and the anelastic power law coefficient (β) are related by:

$$Q = \frac{1 + \beta}{1 - \beta} \qquad (4)$$

Figure 20:
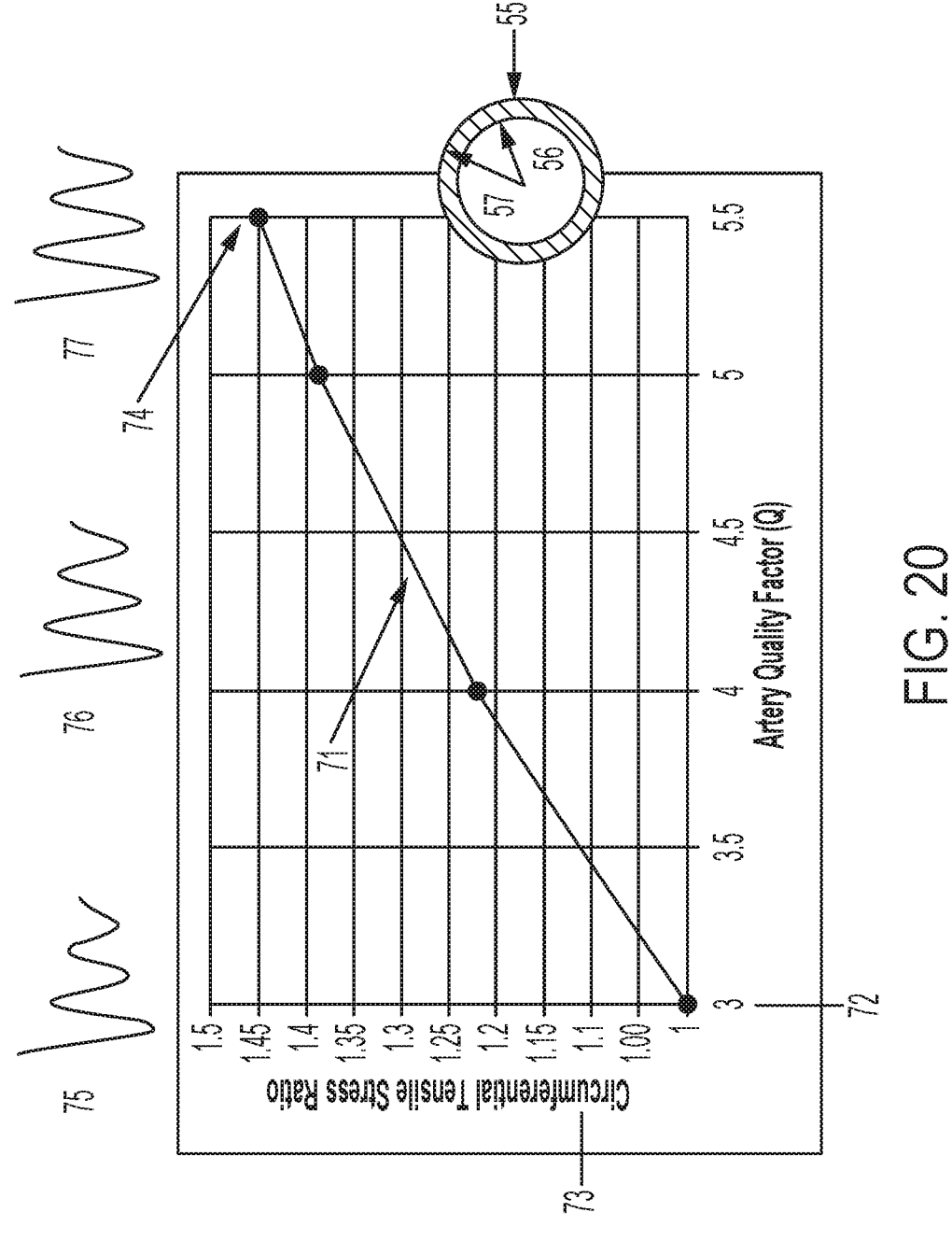
FIG. 20 is an artery quality factor (Q) plot versus circumferential tensile stress ratio of the inner and outer wall of the thick wall anelastic power model, for quantification of the patient's arterial health status from quantification of the patient's anelastic properties of the arterial blood vessels in the body, according to an example embodiment.

FIG. 20 shows the thick wall anelastic power law model 55, a quantified circumferential tensile stress ratio versus Q plot, with the relationship of the ratio of inner wall to outer wall circumferential tensile stress denoted as 71, for an artery of b/a=2. At a Q=3 denoted at 72, the inner and outer wall circumferential tensile stresses are equal yielding a stress ratio of 1 as shown at 73. If a loss of anelasticity of the artery were to occur to increase the artery's Q value to 5.5, for example, the inner wall circumferential tensile stress is 45% higher than the outer wall circumferential tensile stress corresponding to a tensile stress ratio 1.45 denoted at 74.

A Quality factor value of 3, represents a 33% loss of energy due to the blood vessels anelasticity as the pressure pulse travels along the artery, i.e. during the load/unload (pressurize/depressurize) path experienced by the artery during passage of the arterial pulse along its length. The attenuated waveform for a quality factor Q=3 is shown as 75, for Q=4.25 at 76 and for Q=5.5 at 77. And as shown by 75, 76 and 77, the attenuation is only slightly changed for the blood vessel anelasticity Quality factor changing from 3, to 4.25 and to 5.5 respectively. A Q value of 4.25 represents a 23.5% loss of energy due to the blood vessels anelasticity and a Q of 5.5 represents a 18% loss of energy due to the blood vessels anelasticity as the pressure pulse travels along the artery. The Q factor increasing from 3, to 4.25, and to 5.5, is a change in anelastic energy lost from 33%, 23.5% and 18% respectively, and as such is not much of a significant change in the artery's anelasticity, but results in a significant increase in the artery's inner wall circumferential tensile wall stress. Arterial Q values greater than the healthy value of 3, are typically caused by biological aging, arteriosclerosis, and/or disease. In the case of arteries, a Q>3 leads to increased circumferential tensile stresses at the artery inner wall due to the imposed artery pressure pulse, and can lead to a higher incident of aneurysms.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

EXAMPLE EMBODIMENTS

1. A method of quantifying the blood volume status of a patient in near real time, the method comprising the steps of: Placing a piezoelectric sensor over a blood vessel of the patient; Decompose the non-invasive indirect peripheral pressure waveform (PVW/PAW) history into intrinsic oscillatory modes and summing four of these modes into pressure pulse waveform mode; Compute the amplitude spectral density of the two amplitude peaks of the pressure pulse waveform mode and determine their ratio; and Display the blood volume status of the patient.

2. The method of embodiment 1, wherein the decomposition is of the ensemble empirical mode decomposition form.

3. The method of any of embodiments 1-2, wherein the decomposition, summing of intrinsic modes, and display of amplitude ratios is conducted on a sliding time window so as to be near real time display of the patient's blood volume status.

4. The method of any of embodiments 1-3, wherein the display includes an alert message or signal generated at states indicative of hypovolemia or hypervolemia of the patient's blood volume status.

5. The method of any of embodiments 1-4, wherein an intravenous line in the patient is in connection to a fluid source and the evaluation of the patient's blood volume status controls the rate of fluid flow to the patient.

6. The method of embodiment 5, wherein there the rate of flow of the fluid source is controlled via a pump and the evaluation of the patient's blood volume status controls the operation and rate of fluid flow of the pump.

7. The method of any of embodiments 1-6, wherein the heart rate of the patient is continuously displayed.

8. The method of any of embodiments 1-7, wherein the device includes an accelerometer and the intrinsic oscillatory modes are only summed during periods of low patient motion, to provide an update of the blood volume status and heart rate of the patient.

9. The method of any of embodiments 1-8, wherein the Quality factor of the blood vessels are quantified from the attenuation of the high frequency dissipative shear waveform as decomposed from the PVW/PAW, and its difference from a healthy value of 4.33/3 are displayed.

10. The method of embodiment 9, wherein the Q value displayed is related to either biological aging, disease or stiffening of the patient's blood vessels and the significance of the Q value on the patient's health.

11. The method of any of embodiments 1-10, wherein the ratio of the energy of typically the first four (highest order) intrinsic oscillatory modes of the PVW/PAW to the energy in the pressure pulse mode waveform is displayed and its departure from a healthy value quantifies the stiffening, plaque buildup or disease state of the patient's blood vessels.

12. The method of any of embodiments 1-11, wherein the first two (highest order) intrinsic oscillatory modes of the PVW/PAW are summed and displayed and its departure from a healthy patient state are displayed quantifying the state of edema of the patient.

13. The method of embodiment 12, wherein the ratio of the energy of the summed first two (highest order) intrinsic oscillatory modes of the PVW/PAW to the energy of the pressure pulse waveform mode is displayed and related to the state of edema of the patient.

14. The method of embodiment 13, wherein the ratio of the energy of the summed first two (highest order) intrinsic oscillatory modes of the PVW/PAW to the energy of the third and fourth (next highest order) intrinsic oscillatory mode waveform of the PVW/PAW is displayed and related to the state of edema of the patient.

15. A device for measuring and evaluating the vascular and cardiac conditions of a patient comprising: A piezoelectric sensor placed over the blood vessel of the patient; a processing unit that decomposes the non-invasive peripheral waveform (PVW/PAW) history into intrinsic oscillatory modes and summing four of these modes into a pressure pulse mode waveform; the processing unite further computes the amplitude spectral density of the two amplitude peaks of the pressure pulse mode and determines their ratio; and the processing unit displays the blood volume status of the patient.

16. The device of embodiment 15, wherein the pressure sensor is a strain gage type force sensor.

17. The device of any of embodiments 15-16, wherein the pressure sensor is a capacitor type force sensor.

18. The device of any of embodiments 15-17, wherein the processing unit decomposition of the PVW/PAW is of the empirical mode decomposition form.

19. The device of any of embodiments 15-18, wherein the processing unit decomposition of the PAW is of the ensemble empirical mode decomposition form.

20. The device of any of embodiments 15-19, wherein the processing unit decomposition, summing of intrinsic modes and display of amplitude ratios is conducted on a sliding time window so as to be near real time display of the patient's blood volume status.

21. The device of any of embodiments 15-20, wherein the processing unit display includes an alert message or signal generated at states indicative of hypovolemia or hypervolemia of the patient's blood volume status.

22. The device of any of embodiments 15-21, wherein an intravenous line in the patient is in connection to a fluid source and the processing unit's evaluation of the patient's blood volume status signals to the processing unit to control the rate of fluid flow to the patient.

23. The device of any of embodiments 15-22, wherein there the rate of flow of the fluid source is via a pump and the processing unit's evaluation of the patient's blood volume status signals to the processing unit to control the operation and rate of fluid flow of the pump.

24. The device of any of embodiments 15-23, wherein the processing unit computes the heart rate of the patient and the processing unit continuously displays the heart rate of the patient.

25. The device of any of embodiments 15-24, wherein the device includes an accelerometer and the intrinsic oscillatory modes are only summed during periods of low patient motion, to provide an update of the blood volume status and heart rate of the patient.

26. The device of any of embodiments 15-25, wherein the processing unit computes the Quality factor of the blood vessels from the attenuation of the high frequency dissipative shear waveform as decomposed from the PVW/PAW, and computes and displays the difference of the Quality factor deviating from a heathy value of 4.33/3.

27. The device of any of embodiments 15-26, wherein the processing unit displays the Q value and related to patient data, computes and displays the significance of the Q value on the patient's health.

28. The device of any of embodiments 15-27, wherein the processing unit computes the ratio of the energy of typically the first four (highest order) intrinsic oscillatory modes of the PVW/PAW to the energy in the pressure pulse mode waveform, and the processing unit displays this ratio and its departure from a healthy value to quantify from patient data either the stiffening, plaque buildup or disease state of the patient's blood vessels.

29. The device of any of embodiments 15-28, wherein the processing unit computes and sums typically the first two (highest order) intrinsic oscillatory modes of the PVW/PAW, the processing unit displays this summed waveform and its departure from a healthy patient state are displayed quantifying the state of edema of the patient.

30. The method of embodiment 29, wherein the processing unit computes the ratio of the energy of the summed first two intrinsic oscillatory modes of the PVW/PAW to the energy of the pressure pulse mode waveform, displays this ratio and the state of edema of the patient.

31. The method of embodiment 29, wherein the processing unit computes the ratio of the energy of the summed first two intrinsic oscillatory modes of the PVW/PAW to the energy of the sum of the third and fourth intrinsic oscillatory modes of the PVW/PAW, displays this ratio and the state of edema of the patient.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

What is claimed is:

1. A method comprising:
(a) generating, via a piezoelectric sensor, a signal representing vibrations originating from a blood vessel of a subject;
(b) decomposing the signal into one or more first intrinsic oscillatory modes and one or more second intrinsic oscillatory modes using a Hilbert-Huang transform or an ensemble empirical mode decomposition, wherein the one or more first intrinsic oscillatory modes have respective oscillation frequencies that are less than respective oscillation frequencies of the one or more second intrinsic oscillatory modes;

(c) using the one or more second intrinsic oscillatory modes to determine one or more first mechanical properties of the blood vessel or a tissue adjacent to the blood vessel before a treatment is performed, wherein using the one or more second intrinsic oscillatory modes comprises determining a Q-factor of the one or more second intrinsic oscillatory modes;
(d) determining that the one or more first mechanical properties indicate arteriosclerosis, edema, and/or elevated risk of aneurysm;
(e) providing, via a user interface of a computing device, an indication that the one or more first mechanical properties indicate arteriosclerosis, edema, and/or elevated risk of aneurysm;
(f) performing steps (a)-(c) after the treatment is performed to determine one or more second mechanical properties of the blood vessel or the tissue adjacent to the blood vessel; and
(g) quantifying a change in a state of the blood vessel over time using the one or more first mechanical properties and the one or more second mechanical properties.

2. The method of claim 1, wherein the vibrations comprise vibrations of a wall of the blood vessel produced by a fluid flowing through the blood vessel, produced by wall tension of the blood vessel, or produced by contraction or relaxation of the blood vessel in response to the fluid flowing through the blood vessel.

3. The method of claim 1, wherein the one or more second intrinsic oscillatory modes comprise three to five intrinsic oscillatory modes.

4. The method of claim 1,
wherein the one or more second intrinsic oscillatory modes comprise one to three intrinsic oscillatory modes, the method further comprising:
using the one to three intrinsic oscillatory modes to determine whether the subject has edema.

5. The method of claim 4, wherein the one or more second intrinsic oscillatory modes comprise two intrinsic oscillatory modes.

6. The method of claim 5, wherein the two intrinsic oscillatory modes are the highest order intrinsic oscillatory modes of the signal.

7. The method of claim 1, wherein determining the Q-factor comprises determining a logarithmic decrement of the one or more second intrinsic oscillatory modes.

8. The method of claim 1, wherein using the one or more second intrinsic oscillatory modes comprises determining an anelastic coefficient of the one or more second intrinsic oscillatory modes.

9. The method of claim 1, further comprising:
determining a first amount of energy represented by the one or more first intrinsic oscillatory modes and a second amount of energy represented by the one or more second intrinsic oscillatory modes; and
using the first amount of energy and the second amount of energy to determine whether stiffening or plaque buildup are present in blood vessels of the subject.

10. The method of claim 1, further comprising diagnosing or treating a disorder selected from the group consisting of hypervolemia, hypovolemia, euvolemia, dehydration, heart failure, tissue hypoperfusion, myocardial infarction, hypotension, valvular heart disease, congenital heart disease, cardiomyopathy, pulmonary disease, arrhythmia, drug effects, hemorrhage, systemic inflammatory response syndrome, infectious disease, sepsis, electrolyte imbalance, acidosis, renal failure, hepatic failure, cerebral injury, thermal injury, cardiac tamponade, preeclampsia, eclampsia, and toxicity.

11. The method of claim 1, further comprising diagnosing respiratory distress or hypoventilation due to a condition selected from the group consisting of pneumonia, cardiac disorders, sepsis, asthma, obstructive sleep apnea, hypopnea, anesthesia, pain, or narcotic use.

12. A computing device comprising:

one or more processors;

a piezoelectric sensor;

a user interface; and a computer readable medium storing instructions that, when executed by the one or more processors, cause the computing device to perform functions comprising:

(a) generating, via the piezoelectric sensor, a signal representing vibrations originating from a blood vessel of a subject;

(b) decomposing the signal into one or more first intrinsic oscillatory modes and one or more second intrinsic oscillatory modes using a Hilbert-Huang transform or an ensemble empirical mode decomposition, wherein the one or more first intrinsic oscillatory modes have respective oscillation frequencies that are less than respective oscillation frequencies of the one or more second intrinsic oscillatory modes;

(c) using the one or more second intrinsic oscillatory modes to determine one or more first mechanical properties of the blood vessel or a tissue adjacent to the blood vessel before a treatment is performed, wherein using the one or more second intrinsic oscillatory modes comprises determining a Q-factor of the one or more second intrinsic oscillatory modes;

(d) determining that the one or more first mechanical properties indicate arteriosclerosis, edema, and/or elevated risk of aneurysm;

(e) providing, via the user interface, an indication that the one or more first mechanical properties indicate arteriosclerosis, edema, and/or elevated risk of aneurysm;

(f) performing steps (a)-(c) after the treatment is performed to determine one or more second mechanical properties of the blood vessel or the tissue adjacent to the blood vessel; and (g) quantifying a change in a state of the blood vessel over time using the one or more first mechanical properties and the one or more second mechanical properties.

13. The computing device of claim 12, wherein the one or more second intrinsic oscillatory modes comprise one to three intrinsic oscillatory modes.

14. The computing device of claim 12, wherein the one or more second intrinsic oscillatory modes comprise three to five intrinsic oscillatory modes.

15. A non-transitory computer readable medium storing instructions that, when executed by a computing device, cause the computing device to perform functions comprising:

(a) generating, via a piezoelectric sensor, a signal representing vibrations originating from a blood vessel of a subject;

(b) decomposing the signal into one or more first intrinsic oscillatory modes and one or more second intrinsic oscillatory modes using a Hilbert-Huang transform or an ensemble empirical mode decomposition, wherein the one or more first intrinsic oscillatory modes have respective oscillation frequencies that are less than respective oscillation frequencies of the one or more second intrinsic oscillatory modes;

(c) using the one or more second intrinsic oscillatory modes to determine one or more first mechanical properties of the blood vessel or a tissue adjacent to the blood vessel before a treatment is performed, wherein using the one or more second intrinsic oscillatory modes comprises determining a Q-factor of the one or more second intrinsic oscillatory modes;

(d) determining that the one or more first mechanical properties indicate arteriosclerosis, edema, and/or elevated risk of aneurysm;

(e) providing, via a user interface of the computing device, an indication that the one or more first mechanical properties indicate arteriosclerosis, edema, and/or elevated risk of aneurysm;

(f) performing steps (a)-(c) after the treatment is performed to determine one or more second mechanical properties of the blood vessel or the tissue adjacent to the blood vessel; and (g) quantifying a change in a state of the blood vessel over time using the one or more first mechanical properties and the one or more second mechanical properties.

16. The non-transitory computer readable medium of claim 15, wherein the one or more second intrinsic oscillatory modes comprise one to three intrinsic oscillatory modes.

17. The non-transitory computer readable medium of claim 15, wherein the one or more second intrinsic oscillatory modes comprise three to five intrinsic oscillatory modes.

18. The non-transitory computer readable medium of claim 15, wherein the one or more second intrinsic oscillatory modes comprise one to three intrinsic oscillatory modes, the functions further comprising:

using the one to three intrinsic oscillatory modes to determine whether the subject has edema.

19. The non-transitory computer readable medium of claim 15, wherein the one or more second intrinsic oscillatory modes comprise two intrinsic oscillatory modes.

* * * * *